United States Patent
Varley et al.

(10) Patent No.: US 12,157,759 B2
(45) Date of Patent: Dec. 3, 2024

(54) METHOD OF TREATING BREAST CANCER

(71) Applicants: HudsonAlpha Institute for Biotechnology, Huntsville, AL (US); The UAB Research Foundation, Birmingham, AL (US)

(72) Inventors: Katherine E Varley, Salt Lake City, UT (US); Richard M Myers, Huntsville, AL (US); Brian S Roberts, Huntsville, AL (US); Jason Gertz, Huntsville, AL (US); Donald J Buchsbaum, Birmingham, AL (US); Andres Forero-Torres, Birmingham, AL (US); Albert F LoBuglio, Birmingham, AL (US)

(73) Assignees: The UAB Research Foundation, Birmingham, AL (US); HudsonAlpha Institute for Biotechnology, Huntsville, AL (US)

( * ) Notice: Subject to any disclaimer, the term of this patent is extended or adjusted under 35 U.S.C. 154(b) by 542 days.

(21) Appl. No.: 16/552,836

(22) Filed: Aug. 27, 2019

(65) Prior Publication Data

US 2019/0375806 A1 Dec. 12, 2019

Related U.S. Application Data

(60) Division of application No. 15/354,423, filed on Nov. 17, 2016, now abandoned, which is a continuation of application No. 13/828,901, filed on Mar. 14, 2013, now abandoned.

(60) Provisional application No. 61/714,781, filed on Oct. 17, 2012, provisional application No. 61/713,549, filed on Oct. 14, 2012.

(51) Int. Cl.
*C07K 14/47* (2006.01)
*G01N 33/574* (2006.01)

(52) U.S. Cl.
CPC .......... *C07K 14/47* (2013.01); *C07K 14/4748* (2013.01); *G01N 33/57415* (2013.01)

(58) Field of Classification Search
CPC ................ C07K 14/47; C07K 14/4748; G01N 33/57415
See application file for complete search history.

(56) References Cited

U.S. PATENT DOCUMENTS

2007/0083334 A1  4/2007  Mintz
2009/0221437 A1  9/2009  Harkin

FOREIGN PATENT DOCUMENTS

| EP | 1580263 | 9/2005 | |
|---|---|---|---|
| WO | 2008093323 | 8/2008 | |
| WO | WO-2008093323 A2 * | 8/2008 | ............. C07K 14/47 |
| WO | WO-2012012141 A1 * | 1/2012 | ........ A61K 47/48361 |

OTHER PUBLICATIONS

Myers et al. (Global Genomic Analysis of Prostate, Breast and Pancreatic Cancer 52 pages, Oct. 1, 2012).*
Maughan et al.(American Family Physician 81(11): 1339-1346, Jun. 1, 2010).*
Park et al. (Annals of Oncology 21: 488-492, 2010).*
Two cover sheets to Myers et al. (Global Genomic Analysis of Prostate, Breast and Pancreatic Cancer 52 pages, Oct. 1, 2012).*
Christen, U., et al. "Immune response to a recombinant human TNFR55-IgG1 fusion protein: Auto-antibodies in rheumatoid arthritis (RA) and multiple sclerosis (MS) patients have neither neutralizing nor agnosit activities" Human Immunology 60(9): 774-790; Sep. 1999.
Del Monaco, S., et al. "Epithelial sodium channel in a human trophoblast cell line (BeWo)." J. of Membrane Biology 223(3): 127-139, Jun. 2008.
Stanke, F., et al. "The TNF alpha receptor TNFRSF1A and genes encoding the amiloride-sensitive sodium channel ENaC as modulators in cystic fibrosis" Human Genetics 119(3): 331-343; Apr. 2006.
Kimura, K., et al. "Diversification of transcriptional modulation: Large-scale identification and characterization of putative alternative promoters of human genes" Genome Research 16:55-65; 2006. Accession No. DA950392 from Kimura et al., (4), 2006.

* cited by examiner

*Primary Examiner* — Alana Harris Dent
(74) *Attorney, Agent, or Firm* — Stephen H. Hall; Bradley Arant Boult Cummings LLP

(57) ABSTRACT

The present disclosure provides for and relates to novel fusion proteins and polypeptides expressed by breast cancer and other cancer cells, and to compositions, materials and methods for detecting, characterizing and treating said breast and other cancers. In one embodiment, the fusion polypeptides are read-through fusion transcripts.

16 Claims, 4 Drawing Sheets
Specification includes a Sequence Listing.

a

CTSD-IFITM10

SCNN1A-TNFRSF1A b c d e

METHOD OF TREATING BREAST CANCER

CROSS-REFERENCE TO RELATED APPLICATIONS

This application is a division of U.S. patent application Ser. No. 15/354,423, filed 17 Nov. 2016. U.S. patent application Ser. No. 15/354,423 was a continuation of U.S. patent application Ser. No. 13/828,901 filed Mar. 14, 2013 (abandoned) which in turn claimed priority to U.S. Provisional Application No. 61/713,549 filed Oct. 14, 2012 and 61/714,781 filed Oct. 17, 2012.

STATEMENT OF GOVERNMENT INTEREST

This invention was made with government support under grant numbers CA089019 awarded by the National Institutes of Health and W81XWH-10-1-0790 awarded by the Army Medical Research and Materiel Command. The government has certain rights in the invention.

FIELD OF THE DISCLOSURE

The present disclosure provides for and relates to novel fusion proteins and polypeptides expressed by breast cancer and other cancer cells, and to compositions, materials and methods for detecting, characterizing and treating said breast and other cancers. In one embodiment, the fusion polypeptides are read-through fusion transcripts.

BACKGROUND

Fusion genes with oncogenic activity were first identified in hematologic malignancies, where chromosomal translocations frequently join two genes that result in an aberrant protein product (1, 2). These fused genes have been valuable prognostic markers and therapeutic targets (3). The therapeutic value of identifying fusion genes is exemplified by the development of selective inhibitors targeted to the ABL kinase involved in the BCR-ABL fusion that is present in 95% of patients with chronic myelogenous leukemia (1, 2, 4). Most recurrent fusion genes have been identified in leukemias, lymphomas, and soft tissue sarcomas where cytogenetic approaches to detect chromosomal aberrations using spectral karyotyping, fluorescent in situ hybridization, and flow cytometry have been developed (5). Cytogenetic approaches to detect fusion genes in the more common forms of cancer, epithelial tumors, are hampered by the poor chromosome morphology, complex karyotypes, and cellular heterogeneity that typify these tumors, although it has been posited that fusion genes are likely drivers of oncogenesis in these tumors as well (3, 5, 6). Until recently, the most prevalent recurrent fusion genes identified in breast cancer were the ETV6-NTRK3 fusion in secretory breast carcinoma, a rare subtype of infiltrating ductal carcinoma (7) and the MYB-NFIB fusion in adenoid cystic carcinomas, another rare form of breast cancer (8). Recently, genome-wide microarray profiling, whole genome sequencing and whole transcriptome sequencing have made it possible to systematically identify fusion genes in solid tumors. With these methods, recurrent fusions that contribute to malignancy have been identified in prostate cancer (e.g. TMPRSS2 fused to ETS family transcription factors (9-11)), in lung cancer (EML4-ALK (12)), and in breast cancer (MAST kinases fused to NOTCH family genes (13)). New technologies and informatics approaches are enabling the identification of recurrent fusion genes in more common epithelial cancers that may serve as valuable biomarkers and drug targets (13-19).

In addition to fusion genes created by genomic rearrangements, fusion transcripts created by cis- and trans-splicing of mRNA, in the absence of a DNA rearrangements, have been detected by sequencing cDNA clone libraries and performing RNA-seq (20). These chimeric RNAs have been detected at low levels in expressed sequence tag (EST) libraries (21-23) and low levels across benign and malignant samples (6, 20, 24). One particularly prevalent class of chimeric RNAs involves adjacent genes in the same coding orientation that are spliced together to form an in-frame chimeric transcript that spans both genes. In recent literature, these have been referred to as read-through gene fusions, transcription-induced chimeras, co-transcription of adjacent genes coupled with intergenic splicing (CoTIS), or conjoined genes. Several of these read-through fusion transcripts have been identified specifically in prostate cancer and are associated with cellular proliferation and disease progression (25-33). Recurrent read-through transcripts have not yet been characterized in breast cancer.

In 2012, it is estimated that among U.S. women there will be over 225,000 new cases of breast cancer with over 39,000 deaths due to breast cancer. As such, there is a high unmet need for better and more reliable methods of diagnosing and treating breast cancer as well as other cancers. The present disclosure provides three recurrent read-through fusion transcripts encoding various polypeptides associated with breast cancer.

SUMMARY

Figure 1:
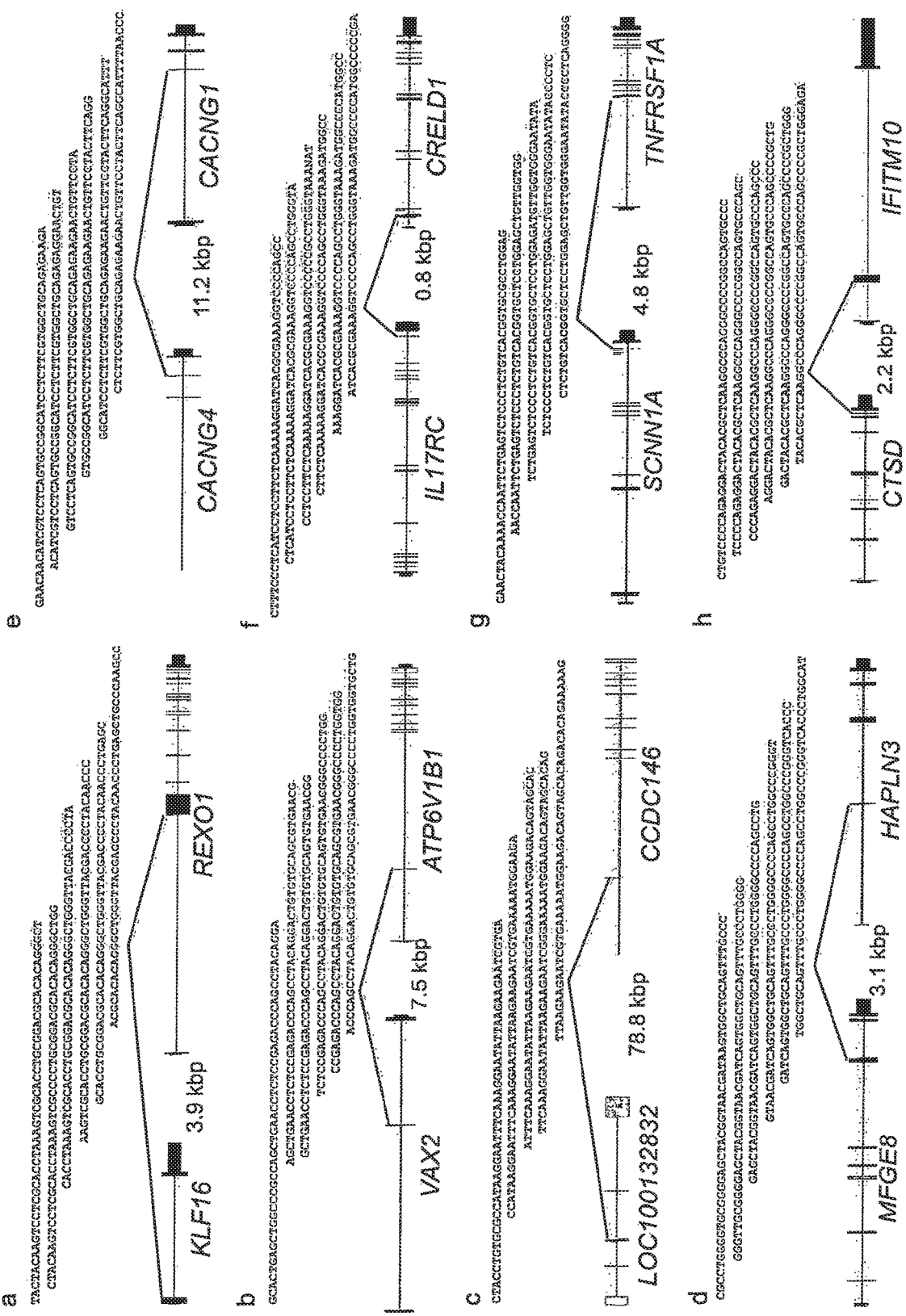
FIG. 1 shows eight (8) read-through fusion transcripts detected in more than two (2) breast tissue samples using paired-end RNA-seq. These read-through fusions were breast-tissue specific, and not detected in other non-neoplastic human tissues sequenced by the Illumina Human Body Map 2.0 project. The exon structure of the 5' fusion partner is depicted on the left, and the exon structure of the 3' fusion partner is depicted on the right. The fusion transcripts use endogenous splice sites and black lines indicate which exons flank the fusion junction to result in the chimeric transcript. RNA-seq reads that span the fusion junction are depicted above the gene models. The intergenic chromosomal distance between the fusion partners is denoted in kilobase pairs (kbp). The five (5) read-through fusion transcripts depicted in a, b, c, d and e were detected in both breast cancer specimens and non-cancer breast tissue. Three (3) read-through fusion transcripts significantly associated with breast cancer are depicted in f, g and h.

The present disclosure provides novel fusion transcripts and novel fusion polypeptides expressed therefrom. In one embodiment, such fusion transcripts and fusion polypeptides are expressed in breast cancer. In one embodiment, such fusion transcripts and fusion polypeptides exhibit differentially increased expression in breast cancer and as compared to normal breast cells and other neoplastic tissue. In one embodiment, such fusion transcripts and fusion polypeptides exhibit differentially increased expression in human breast cancer as compared to normal human breast cells and other human neoplastic tissue. In one embodiment, such fusion transcripts and fusion polypeptides exhibit differentially increased expression in estrogen receptor positive (ER+) breast cancer primary tumors and triple negative breast cancer (TNBC) primary tumors as compared to normal breast cells and other neoplastic tissue. In one embodiment, such fusion transcripts are significantly associated with human breast cancer.

The present disclosure also provides nucleic acids encoding the novel polypeptides or fragments of the polypeptides. Also provided are probes and primers used to amplify and detect nucleic acids encoding the novel fusion junction polypeptides or fragments of the polypeptides.

The nucleic acids may be double stranded, single stranded, RNA, DNA, variants or synthetic variants thereof. In one embodiment, the nucleic acids encode the fusion junction polypeptides generated by the read through transcripts of IL17RC-CRELD1, SCNN1A-TNFRSF1A or CTSD-IFITM10. In one embodiment, the present disclosure provides a nucleic acid as in SEQ ID NO: 1 encoding the fusion polypeptide from a read through transcript of IL17RC-CRELD1. In one embodiment, the present disclosure provides a nucleic acid as in SEQ ID NO: 2 encoding a fusion polypeptide from a read through transcript of SCNN1 A-TNFRSF1A. In one embodiment, the present disclosure provides a nucleic acid as in SEQ ID NO 3 encoding a fusion polypeptide from a read through transcript of CTSD-IFITM10.

In one embodiment, the fusion transcripts are the result of splicing of mRNA without DNA rearrangements and the fusion polypeptides are expressed from such fusion transcripts. In one embodiment the fusion transcripts are the result of fusion between mRNA coding for the proteins IL17RC and CRELD1 polypeptides, the SCNN1A and TNFRSF1A polypeptides and/or the CTSD and IFITM10 polypeptides resulting in the fusion of the proteins IL17RC-CRELD1, SCNN1A-TNFRSF1A or CTSD-IFITM10. In one embodiment, the present disclosure provides a fusion polypeptide from a read through transcript of IL17RC-CRELD1 as in SEQ ID. NO: 4 or SEQ ID. NO. 5, or fragments thereof. In one embodiment, the present disclosure provides a fusion polypeptide from a read through transcript of SCNN1A-TNFRSF1A as in SEQ ID. NO: 6, or a fragment thereof. In one embodiment, the present disclosure provides a fusion polypeptide from a read through transcript of CTSD-IFITM10 as in SEQ ID. NO: 7, or a fragment thereof.

Also provided are vectors comprising the nucleic acids of the present disclosure. In one embodiment, the vector is an expression vector. In one embodiment, the expression vector comprises the nucleic acid sequence of SEQ ID NO: 1 or a fragment thereof. In another embodiment, the expression vector comprises the nucleic acid sequence of SEQ ID NO: 2, or a fragment thereof. In yet another embodiment, the expression vector comprises the nucleic acid sequence of SEQ ID NO: 3, or a fragment thereof. Also provided is a host cell comprising the vector or the expression vector.

Also provided are recombinant host cells that express the fusion polypeptides of the present disclosure on the cell's surface or that excrete the polypeptides to the exterior of the cell. In one embodiment the recombinant host cell expresses or excretes the polypeptide of SEQ ID NO: 4 or SEQ ID NO: 5, or variants or fragments thereof. In one embodiment the recombinant host cell expresses or excretes the polypeptide of SEQ ID NO: 6 or a variant or a fragment thereof. In one embodiment the recombinant host cell expresses or excretes the polypeptide of SEQ ID NO: 7 or a variant or a fragment thereof.

In some embodiments the invention provides antigen-binding agents including antibodies that specifically bind to the fusion polypeptides and fusion proteins, the antigen binding agents preferably having a greater affinity for the fusion polypeptides and proteins than for either of the fusion partners that make up the fusion protein. The antibodies of the invention may be monoclonal or polyclonal antibodies. In some embodiments the antibodies are chimeric, humanized, or human antibodies. In some embodiments the antibodies are single chain antibodies or Fab fragments.

In some aspects the invention provides an isolated antigen binding agent that specifically binds to a IL17RC-CRELD1, SCNN1A-TNFRSF1A or CTSD-IFITM10 fusion polypeptide. In some preferred embodiments the binding agent is a monoclonal antibody. In some aspects the invention provides an isolated monoclonal antibody or other antigen binding agent that specifically binds to a IL17RC-CRELD1, SCNN1A-TNFRSF1A or CTSD-IFITM10 fusion polypeptide, wherein the antigen binding agent specifically binds to a IL17RC-CRELD1 fusion polypeptide of SEQ ID NO: 4 or SEQ ID NO: 5, a SCNN1A-TNFRSF1A fusion polypeptide of SEQ ID NO: 6 or CTSD-IFITM10 fusion polypeptide of SEQ ID NO: 7. In some aspects the invention provides a monoclonal antibody wherein the antibody binds a IL17RC-CRELD1, SCNN1A-TNFRSF1A or CTSD-IFITM10 fusion polypeptide protein with an affinity less than 1 nM.

In some embodiments the antibody or other binding agent specifically binds to the IL17RC-CRELD1, SCNN1A-TNFRSF1A or CTSD-IFITM10 fusion polypeptides, or to fragments thereof, expressed on the surface of a recombinant cell.

Also provided is a hybridoma capable of producing the antibodies of the present invention. Also provided is a method of making the antibodies or other antigen binding agents comprising culturing a host cell under conditions that allow the host cell to express the antigen binding agent.

The invention provides methods of detecting nucleic acid sequences that can be used for diagnosing, characterizing, and treating tumors in an individual with IL17RC-CRELD1, SCNN1A-TNFRSF1A or CTSD-IFITM10 fusion transcript or in need of treatment from a disease resulting, at least in part from, the expression or the differentially increased expression of a IL17RC-CRELD1, SCNN1A-TNFRSF1A or CTSD-IFITM10 fusion transcript."

The invention provides methods of making antibodies that can be used for diagnosing, characterizing, and treating tumors in an individual with IL17RC-CRELD1, SCNN1A-TNFRSF1A or CTSD-IFITM10 fusion polypeptide or in need of treatment from a disease resulting, at least in part from, the expression or the differentially increased expression of a IL17RC-CRELD1, SCNN1A-TNFRSF1A or CTSD-IFITM10 fusion polypeptide.

The invention provides methods of making antibodies that can be used for detecting, characterizing, and treating tumors comprising screening a library of antibodies expressed on phage, phagemids, ribosomes, or other particles with a IL17RC-CRELD1, SCNN1A-TNFRSF1A or CTSD-IFITM10 fusion polypeptide. In some embodiments the polypeptide used to screen the library is expressed on the surface of a recombinant cell. The resulting antibodies may be isolated using standard methods known in the art. In some embodiments the library is a library of human antibodies or humanized antibodies.

Also provided are isolated nucleic acid molecules comprising a polynucleotide sequence encoding the light chain variable domain, the heavy chain variable domain, or both, of the antibodies or other antigen binding agents of the invention. In one embodiment, the polynucleotide comprises a light chain variable sequence, and a heavy chain variable sequence.

In some aspects the invention provides bispecific antibodies or other binding agents in which a first antigen-binding site binds an epitope on a first fusion partners and a second antigen-binding site binds an epitope on a second fusion partner. For example, a bispecific antibody could comprise a first antigen-binding site that binds CTSD and a second antigen-binding site that binds IFITM10.

In some aspects the invention provides antibodies with enhanced effector functions. In other aspects the invention provides antibodies conjugated to a toxin or other therapeutic agent. In some aspects of the invention the toxin or other therapeutic agent is joined to the antibody by means of a cleavable or non-cleavable linker.

In another aspect, the invention relates to the use of a siRNA construct that is targeted to the IL17RC-CRELD1, SCNN1A-TNFRSF1A or CTSD-IFITM10 fusion polypeptide/nucleotide in the treatment of cancer, such as breast cancer. The siRNA constructs are set forth in SEQ ID NOS. 15-22 respectively and variants thereof, including nucleic acid sequences 90, 91, 92, 93, 94, 95, 96, 97, 98 and 99% identical to one of SEQ ID. NOS 15-22, should be considered with the scope of this disclosure. In one embodiment the siRNA constructs silence or down regulate the expression of the IL17RC-CRELD1, SCNN1A-TNFRSF1A or CTSD-IFITM10 fusion polypeptide/nucleotide. According to still another aspect of the present invention is a method for increasing the efficacy of cancer therapy in a subject, the method comprising: administering to a subject in need of an effective amount of an siRNA construct directed to a IL17RC-CRELD1, SCNN1A-TNFRSF1A or CTSD-IFITM10 fusion polypeptide/nucleotide, wherein said subject is also being administered a cancer therapy selected from the group consisting of small-molecule drugs, angiogenesis inhibitors, tumor vaccine, chemotherapy, immunotherapy, radiation therapy, gene therapy and combinations thereof.

Also provided is a pharmaceutical composition comprising the antibodies or other antigen binding proteins of the present invention. In one embodiment the pharmaceutical composition comprises a human or humanized antibody.

In some embodiments the invention provides methods useful to detect and characterize breast cancer and other types of tumors. Some aspects of the invention comprise detecting the expression or the differentially increased expression of a fusion polypeptide according to the invention in cells from the tumor. In some embodiments the fusion protein detected is selected from: (a) SEQ ID NO: 4 or SEQ ID NO: 5, or a fragment thereof, (b) SEQ ID NO: 6, or a fragment thereof, or (c) SEQ ID NO: 7, or a fragment thereof.

In some aspects of the invention expression of the fusion polypeptide is detected at the RNA level. In other aspects of the invention expression of the fusion polypeptide is detected at the level of protein synthesis. In some aspects of the invention expression of the fusion polypeptide is detected through the use of an antibody that specifically binds the polypeptide.

In some embodiments, antibodies or other antigen binding agents of the invention are useful to treat breast and other cancers or for preparing a pharmaceutical composition for use in treating breast and other cancers. In one embodiment, the invention includes a method of inhibiting proliferation of cells expressing a IL17RC-CRELD1, SCNN1A-TNFRSF1A or CTSD-IFITM10 fusion polypeptide. In one embodiment, the method comprises contacting the cells with a composition comprising an antigen binding agent that specifically binds to a IL17RC-CRELD1, SCNN1A-TNFRSF1A or CTSD-IFITM10 fusion polypeptide. In some aspects the antigen binding agent is an antibody according to the invention. In another embodiment, the invention provides a method of inhibiting the expression of a IL17RC-CRELD1, SCNN1A-TNFRSF1A or CTSD-IFITM10 fusion polypeptide. Some aspects of the invention are directed to a method of preparing a pharmaceutical composition for use in treating a patient with cancer, wherein the composition comprises an antigen binding agent or bispecific antibody that specifically binds to a IL17RC-CRELD1, SCNN1A-TNFRSF1A or CTSD-IFITM10 fusion polypeptide. In some aspects the antigen binding agent is an antibody according to the invention.

In some aspects of the invention the patient is treated with antibodies having enhanced effector functions. In some aspects of the invention the patient is treated with antibodies conjugated to a toxin or other therapeutic agent. In some aspects of the invention the therapeutic agent is joined to the antibody by means of a cleavable or non-cleavable linker. In some aspects of the invention treatment is administered after detection of the expression of an IL17RC-CRELD1, SCNN1A-TNFRSF1A or CTSD-IFITM10 fusion polypeptide in cells from the individual.

DETAILED DESCRIPTION

While the invention has been described with respect to a limited number of embodiments, those skilled in the art, having benefit of this disclosure, will appreciate that other embodiments can be devised which do not depart from the scope of the invention as disclosed here.

The present disclosure identifies and provides novel fusion protein and polypeptides expressed by breast cancer cells and other cancer cells. In another aspect, the present disclosure provides novel nucleic acid molecules that encode the fusion polypeptides. In yet another aspect, the present disclosure provides antigen binding agents, including antibodies that specifically bind to the fusion polypeptides. In another aspect, the present disclosure provides methods of diagnosing and treating breast cancer or other cancers by detecting the presence of the novel fusion polypeptides in an individual. In yet another aspect, the present disclosure provides for methods of treating breast cancers or other cancers in an individual by inhibiting the expression of the fusion polynucleotides and/or polypeptides by the breast cancer cells or other cancer cells In yet another aspect, the present disclosure provides for methods of treating breast cancers or other cancers in an individual by contacting a cell expressing the fusion polypeptide with a composition comprising an antigen binding agent that binds to the fusion polypeptide. In yet another aspect, the present disclosure provides for methods of treating breast cancers or other cancers in an individual by inhibiting the expression of the fusion protein polypeptides by the breast cancer cells or other cancer cells.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al, Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The term "antibody" is used in the broadest sense and includes, for example, an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include Fab, Fab', F(ab')$_2$, Fd, Fv, and domain antibodies (dAbs), and complementarity determining region (CDR) fragments, single-chain antibodies (scFv), diabodies, triabodies, tetrabodies, and polypeptides that contain at least a portion of an immunoglobulin that is sufficient to confer specific antigen binding to the polypeptide. Antibody includes a human antibody, a humanized antibody, chimeric antibody, a monoclonal antibody, a polyclonal antibody, a recombinant antibody, an antigen-binding antibody fragment, a single chain antibody, a maxibody (scFv fused by a linker or direct attachment to an Fc or an Fc fragment), a diabody, a triabody, a tetrabody, a Fab fragment, an F(fa')x fragment, a domain antibody, an IgD antibody, an IgE antibody, and IgM antibody, and IgG1 antibody, and IgG2 antibody, and IgG3 antibody, and IgG4 antibody, and IgG4 antibody having at least one mutation in the hinge region that alleviates a tendency to for intra H-chain disulfide bonds.

The term "antigen binding agent" refers to a natural or non-natural molecule, in one embodiment a proteinaceous molecule, that specifically binds to a target, such as for example a fusion polypeptide of the present disclosure. The term "specific binding" or "specifically binds" refers to the ability of an antigen binding agent to bind to a target with greater affinity (strength of binding) than it binds to a non-target. In certain embodiments, specific binding refers to binding to a target with an affinity that is at least 10, 50, 100, 250, 500, or 1000 fold greater than the affinity for a non-target. In certain embodiments, affinity is determined by an affinity ELISA assay, by a BIAcore assay, by a kinetic method, or by an equilibrium/solution method. Affinity can be expressed in terms of the dissociation constant $K_d$. Examples of antigen binding agents includes, but are not limited to proteins, peptides, nucleic acids, carbohydrates, lipids, and small molecule compounds. In some embodiments the antigen binding agent is an antigen binding protein; in some embodiments, the antigen binding agent is an antibody.

The term "antigen binding protein" refers to a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer (see for example, Korndorfer et al, 2003, Proteins: Structure, Function, and Bioinformatics, Volume 53, Issue 1: 121-129; Roque et al, 2004, Biotechnol. Prog. 20:639-654). In addition, peptide antibody mimetics ("PAMs") can be used, as well as scaffolds based on antibody mimetics utilizing fibronection components as a scaffold. Antigen binding proteins further include peptibodies. The term "peptibody" refers to a molecule comprising an antibody Fc domain attached to at least one peptide. The production of peptibodies is generally described in PCT publication WO 00/24782. Antigen binding proteins further include nonimmunoglobulin avidity multimers or "avimers," which are multidomain proteins derived from the A-domains as found in various cell surface receptors. Avimers can be generated by the sequential selection of individual binding domains, each of which recognize a different epitope, and can therefore bind multiple sites on a target or even multiple targets. (see, for example, Silverman, J. et al. Nat. Biotechnol. 23, 1556-1561, 2005).

The term "antigen binding site" refers to the portion of an antigen binding agent that contains amino acid residues or other moieties that interact with an antigen and contribute to the antigen binding protein's specificity and affinity for the antigen. For an antibody that specifically binds to its antigen, this will include at least part of at least one of its CDR domains. An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody may have two different binding sites. An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. The variable regions of each light/heavy chain pair form the antibody binding site such that an intact immunoglobulin has two binding sites. Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. (Sequences of Proteins of Immunological Interest, $5^{th}$ Ed., US Dept. of Health and Human Services, PHS, NIH, NIH Publication no. 91-3242, 1991). Intact antibodies include polyclonal, monoclonal, chimeric, humanized or fully human antibodies having full length heavy and light chains.

The term "chimeric antibody" refers to an antibody that contains one or more regions from one antibody and one or more regions from one or more other antibodies. A "CDR grafted antibody" is an antibody comprising one or more CDRs derived from an antibody of a particular species or isotype and the framework of another antibody of the same or different species or isotype.

The term "down regulated," as it refers to genes inhibited by the subject RNAi method, refers to a diminishment in the level of expression of a gene(s) in the presence of one or more siRNA construct(s) when compared to the level in the absence of such siRNA construct(s). The term "down regulated" is used herein to indicate that the target gene expression is lowered by 1-100%. For example, the expression may be reduced by about 10, 20, 30, 40, 50, 60, 70, 80, 90, 95, or 99%.

The term "epitope" refers to that portion of the antigen that an antigen binding agent recognizes. In the case of an antibody that binds a protein target, an "epitope" is the antigenic site on the protein that is recognized by the antibody, i.e., the minimum molecular structure within the protein target to which the antibody binds. Epitopes on proteins may be continuous (comprising a segment of continuous amino acids from the primary amino acid sequence) or non-continuous (comprising amino acids that are not continuous in the primary protein sequence but which are in close proximity in the three-dimensional folded protein).

The term "Fab fragment" refers to a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain.

The term "gene silencing" refers to the suppression of gene expression, e.g., transgene, heterologous gene and/or endogenous gene expression. Gene silencing may be mediated through processes that affect transcription and/or through processes that affect post-transcriptional mechanisms. Gene silencing may occur when siRNA initiates the degradation of the mRNA of a gene of interest in a sequence-specific manner via RNA interference (for a review, see Brantl, 2002, Biochim. Biophys. Acta, 1575(1-3): 15-25). Gene silencing may be allele-specific wherein specific silencing of one allele of a gene occurs.

The term "host cell" refers to a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23: 175), L cells, CI 27 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "human antibody" includes all antibodies that have one or more variable and constant regions derived from human immunoglobulin sequences. In one embodiment, all of the variable and constant domains are derived from human immunoglobulin sequences (a fully human antibody). Human antibodies may be prepared in a variety of ways, including immunization of a mouse that is genetically modified to express human antibodies. One can engineer mouse strains deficient in mouse antibody production with large fragments of the human Ig loci in anticipation that such mice would produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains may yield high affinity fully human antibodies against any antigen of interest, including human antigens. Using the hybridoma technology, antigen-specific human MAbs with the desired specificity may be produced and selected. Certain exemplary methods are described in WO 98/24893, U.S. Pat. No. 5,545,807, EP 546073B1, and EP 546073A1. Human antibodies can also be prepared by panning human antibody libraries expressed on phage, phagemids, ribosomes, or other particles.

The term "humanized antibody" refers to an antibody that has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of methods for making humanized antibodies may be found in U.S. Pat. Nos. 6,054,297, 5,886,152 and 5,877,293.

The term "individual" or "patient" as used herein refers to any animal, including mammals, such as, but not limited to, mice, rats, other rodents, rabbits, dogs, cats, swine, cattle, sheep, horses, or primates, or humans. The term may specify male or female or both, or exclude male or female.

The term "in need of prevention" as used herein refers to a judgment made by a caregiver that a patient requires or will benefit from prevention. This judgment is made based on a variety of factors that are in the realm of a caregiver's expertise, and may include the knowledge that the patient may become ill as the result of a disease state that is treatable by a compound or pharmaceutical composition of the disclosure.

The term "in need of treatment" as used herein refers to a judgment made by a caregiver that a patient requires or will benefit from treatment. This judgment is made based on a variety of factors that are in the realm of a caregiver's expertise, and may include the knowledge that the patient is ill as the result of a disease state that is treatable by a compound or pharmaceutical composition of the disclosure.

The term "isolated" or "purified" molecule (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" or "purified" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "monoclonal antibodies" refers to a collection of antibodies encoded by the same nucleic acid molecule. In certain embodiments, monoclonal antibodies are produced by a single hybridoma or other cell line, or by a transgenic mammal. Monoclonal antibodies typically recognize the same epitope. The term "monoclonal" is not limited to any particular method for making an antibody.

The term "multispecific antibody" refers to an antibody wherein two or more variable regions bind to different epitopes. The epitopes may be on the same or different targets. In certain embodiments, a multispecific antibody is a "bispecific antibody," which recognizes two different epitopes on the same or different antigens.

The terms "peptide," "polypeptide," and "protein" each refer to a molecule comprising two or more amino acid residues joined to each other by peptide bonds. These terms encompass, e.g., native and artificial proteins, protein fragments and polypeptide analogs such as muteins, variants, and fusion proteins of a protein sequence as well as post-translationally, or otherwise covalently or non-covalently, modified proteins.

The term "polyclonal antibody" refers to a heterogeneous mixture of antibodies that bind to different epitopes of the same antigen.

The terms "polynucleotide" and "nucleic acid" are used interchangeably throughout and include DNA molecules (e.g., cDNA or genomic DNA), RNA molecules (e.g., mRNA, siRNA), analogs of the DNA or RNA generated using nucleotide analogs (e.g., peptide nucleic acids, and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector.

The terms "prevent", "preventing", "prevention" "suppress", "suppressing" and suppression as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be useful.

The term "single-chain antibody" (scFv) refers to an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al, 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al, 1993, Proc. Natl. Acad. Sci. USA 90:6444-48, and Poljak et al, 1994, Structure 2: 1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

The term "RNA interference (RNAi)" refers to the process of sequence-specific, posttranscriptional gene silencing initiated by siRNA. During RNAi, siRNA induces degradation of target mRNA with consequent sequence-specific inhibition of gene expression.

The term "small interfering" or "short interfering RNA" or "siRNA" refers to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. siRNA is "targeted" to a gene in that the nucleotide sequence of the duplex portion of the siRNA is substantially complementary to a nucleotide sequence of the targeted gene. The siRNA sequence duplex needs to be of sufficient length to bring the siRNA and target RNA together through complementary base-pairing interactions. The siRNA of the invention may be of varying lengths. The length of the siRNA is preferably greater than or equal to ten nucleotides and of sufficient length to stably interact with the target RNA; specifically 10-30 nucleotides; more specifically any integer between 10 and 30 nucleotides, such as 10, 11, 12, 13, 14, 15, 16, 17, 18, 19, 20, 21, 22, 23, 24, 25, 26, 27, 28, 29, and 30. By "sufficient length" is meant a nucleotide of greater than or equal to 10 nucleotides that is of a length great enough to provide the intended function under the expected condition. The term "stably interact" refers to interaction of the small interfering RNA with target nucleic acid (e.g., by forming hydrogen bonds with complementary nucleotides in the target under physiological conditions).

The term "therapeutically effective amount", in reference to the treating, preventing or suppressing of a disease state, refers to an amount of a compound either alone or as contained in a pharmaceutical composition that is capable of having any detectable, positive effect on any symptom, aspect, or characteristics of the disease state/condition. Such effect need not be absolute to be beneficial.

The terms "treat", "treating" and "treatment" as used herein refers to administering a compound either alone or as contained in a pharmaceutical composition after the onset of clinical symptoms of a disease state so as to reduce or eliminate any symptom, aspect or characteristic of the disease state. Such treating need not be absolute to be useful.

The term "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least about 40%, 50%, 60%, 70%, 80%, 90%, 95%, 96%, 97%, 98%, to 99%0/sequence identity to the native (endogenous) nucleotide sequence.

The term "vector" refers to a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide and may comprise an expression control element which will control, at least in part, the expression of the polynucleotide. Expression control elements are known in the art and include various promoters.

Isolated Nucleic Acids and Purified Polypeptides

In one aspect, the present disclosure provides novel isolated nucleic acids, including variants and fragments thereof. In one embodiment, the isolated nucleic acids correspond to the fusion transcripts of the present disclosure, or a fragment thereof. In one embodiment, the fusion transcript is the IL17RC-CRELD1 fusion transcript, the SCNN1A-TNFRSF1A fusion transcript or the CTSD-IFITM10 fusion transcript. In one embodiment, the nucleic acid coding for a fragment of the fusion transcript of the present disclosure corresponds to a junction region (a region containing sequence from both the 5' and 3' fusion partners) of a fusion transcript of the present disclosure. In one embodiment, the fusion junction is from the IL17RC-CRELD1 fusion transcript, the SCNN1A-TNFRSF1A fusion transcript or the CTSD-IFITM10 fusion transcript.

In another embodiment, the present disclosure provides novel isolated nucleic acids coding for a fusion polypeptide of the present disclosure or a fragment thereof. In one embodiment, the fusion polypeptide is the IL7RC-CRELD1 fusion polypeptide, the SCNN1A-TNFRSF1A fusion polypeptide or the CTSD-IFITM10 fusion polypeptide. In one embodiment, the nucleic acid coding for a fragment of the fusion polypeptide of the present disclosure is an isolated nucleic acid molecule coding for a junction region (a region containing sequence from both the 5' and 3' fusion partners) of a fusion polypeptide of the present disclosure. In one embodiment, the fusion junction is from the IL17RC-CRELD1 fusion polypeptide, the SCNN1A-TNFRSF1A fusion polypeptide or the CTSD-IFITM10 fusion polypeptide. Such an isolated nucleic acid molecule may code for at least 3, at least 5 or at least 10 amino acid residues of each partner of the fusion polypeptide. In yet another aspect, the present disclosure provides methods for making the isolated nucleic acids and purified polypeptides in an expression system, such as a vector.

In one embodiment, the isolated nucleic acid comprises the sequence of SEQ ID NO: 1, or a fragment thereof. SEQ ID NO: 1 provides the nucleic acid sequence corresponding to the junction region of the IL17RC-CRELD1 fusion transcript. In one embodiment, the isolated nucleic acid comprises the sequence of SEQ ID NO: 8, or a fragment thereof. SEQ ID NO:8 provides the predicted cDNA sequence corresponding to the full length IL17RC-CRELD1 fusion transcript. In one embodiment, the fragment of SEQ ID NO: 8 corresponds to or comprises a junction region of the IL17RC-CRELD1 fusion transcript.

In another embodiment, the isolated nucleic acid comprises the polynucleotide sequence of SEQ ID NO: 2, or a fragment thereof. SEQ ID NO: 2 provides the nucleic acid sequence corresponding to the junction region of the SCNN1A-TNFRSF1A fusion transcript. In one embodiment, the isolated nucleic acid comprises the sequence of SEQ ID NO: 10, or a fragment thereof. SEQ ID NO: 10 provides the predicted cDNA sequence corresponding to the full length SCNN1A-TNFRSF1A fusion transcript. In one embodiment, the fragment of SEQ ID NO: 10 corresponds to or comprises a junction region of the SCNN1A-TNFRSF1A fusion transcript.

In another embodiment, the isolated nucleic acid comprises the polynucleotide sequence of SEQ ID NO: 3, or a fragment thereof. SEQ ID NO: 3 provides the nucleic acid sequence corresponding to the junction region of the CTSD-IFITM10 fusion transcript. In one embodiment, the isolated nucleic acid comprises the sequence of SEQ ID NO: 12, or a fragment thereof. SEQ ID NO: 12 provides the predicted cDNA sequence corresponding to the full length CTSD-IFITM10 fusion transcript. In one embodiment, the fragment of SEQ ID NO: 12 corresponds to or comprises a junction region of the CTSD-IFITM10 fusion transcript.

In another aspect, the present disclosure provides novel isolated prolypeptides. In one embodiment, the present disclosure provides novel isolated fusion polypeptides, or a fragment thereof. In one embodiment, the fusion prolypeptide is the IL17RC-CRELD1 fusion polypeptide, the SCNN1A-TNFRSF1A fusion polypeptide or the CTSD-IFITM10 fusion polypeptide. In one embodiment, the fragment of the fusion polypeptide of the present disclosure is a fragment containing a junction region (a region containing sequence from both the 5' and 3' fusion partners) of a fusion polypeptide of the present disclosure. In one embodiment, the fusion junction is from the IL17RC-CRELD1 fusion polypeptide, the SCNN1A-TNFRSF1A fusion polypeptide or the CTSD-IFITM10 fusion polypeptide. Such polypeptide fragment may contain at least 3, at least 5 or at least 10 amino acid residues of each partner of the fusion polypeptide.

In one embodiment, the isolated fusion polypeptide comprises the amino acid sequence of SEQ ID NO: 4, or a fragment thereof. SEQ ID NO: 4 provides the amino acid sequence corresponding to the junction region of the IL17RC-CRELD1 fusion polypeptide. In another embodiment, SEQ ID NO: 5 provides a different amino acid sequence corresponding to the junction region of the IL17RC-CRELD1 fusion polypeptide. In one embodiment, the isolated fusion polypeptide comprises the amino acid of SEQ ID NO: 9, or a fragment thereof. SEQ ID NO: 9 provides the predicted amino acid sequence corresponding to the full length IL17RC-CRELD1 fusion transcript. In one embodiment, the fragment of SEQ ID NO: 9 corresponds to or comprises a junction region of the IL17RC-CRELD1 fusion transcript. In one embodiment, the isolated fusion polypeptide comprises the amino acid of SEQ ID NO: 13, or a fragment thereof. SEQ ID NO: 13 provides the predicted amino acid sequence corresponding to the full length IL17RC-CRELD1 fusion transcript. In one embodiment, the fragment of SEQ ID NO:13 corresponds to or comprises a junction region of the IL17RC-CRELD1 fusion transcript.

In another embodiment, the isolated fusion polypeptide comprises the amino acid sequence of SEQ ID NO: 6, or a fragment thereof. SEQ ID NO: 6 provides the amino acid sequence corresponding to the junction region of the SCNN1A-TNFRSF1A fusion polypeptide. In one embodiment, the isolated fusion polypeptide comprises the amino acid of SEQ ID NO: 11, or a fragment thereof. SEQ ID NO: 11 provides the predicted amino acid sequence corresponding to the full length SCNN1A-TNFRSF1A fusion transcript. In one embodiment, the fragment of SEQ ID NO: 11 corresponds to or comprises a junction region of the SCNN1A-TNFRSF1A fusion transcript.

In another embodiment, the isolated fusion polypeptide comprises the amino acid sequence of SEQ ID NO: 7, or a fragment thereof. In one embodiment, the isolated fusion polypeptide comprises the amino acid of SEQ ID NO: 14, or fragments thereof. SEQ ID NO: 14 provides the predicted amino acid sequence corresponding to the full length CTSD-IFITM10 fusion transcript incorporating the junction region of SEQ ID NO: 7. In one embodiment, the fragment of SEQ ID NO: 14 corresponds to or comprises a junction region of the CTSD-IFITM10 fusion transcript.

In yet another aspect, the present disclosure provides a method of making the isolated polynucleotides or the purified polypeptides. Any expression system known in the art can be used to make the isolated polynucleotides or the purified polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example $E.\ coli$ or bacilli. Higher eukaryotic cells include insect cells and established cell lines of mammalian origin. Examples of suitable mammalian host cell lines include the COS-7 line of monkey kidney cells (ATCC CRL 1651) (Gluzman et al, 1981, Cell 23:175), L cells, 293 cells, CI 27 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al, 1991, EMBO J. 10: 2821. Appropriate cloning and expression vectors for use with bacterial, fungal, yeast, and mammalian cellular hosts are described by Pouwels et al. {Cloning Vectors: A Laboratory Manual, Elsevier, New York, 1985).

The transformed cells can be cultured under conditions that promote expression of the polypeptide, and the polypeptide recovered by conventional protein purification procedures. One such purification procedure includes the use of affinity chromatography. Polypeptides contemplated for use herein include substantially homogeneous recombinant mammalian antibody polypeptides substantially free of contaminating endogenous materials.

Preparation of Antigen Binding Agents and Proteins

In another aspect, the resent disclosure provides for the making of antigen binding agents and proteins prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Antigen binding proteins may be prepared, and screened for desired properties, by any of a number of known techniques. Certain of the techniques involve isolating a nucleic acid encoding a polypeptide chain (or portion thereof) of an antigen binding protein of interest, and manipulating the nucleic acid through recombinant DNA technology. The nucleic acid may be fused to another nucleic acid of interest, or altered {e.g., by mutagenesis or other conventional techniques) to add, delete, or substitute one or more amino acid residues, for example.

Complementarity determining regions (CDRs) and framework regions (FR) of a given antibody may be identified using the system described by Kabat et al. in Sequences of Proteins of Immunological Interest, $5^{th}$ Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al, 1991, Science 253: 164.

Numerous methods of preparing bispecific antibodies are known in the art, and discussed in, e.g., U.S. patent application Ser. No. 09/839,632, filed Apr. 20, 2001 (incorporated by reference herein). Such methods include the use of hybrid-hybridomas as described by Milstein et al, 1983, Nature 305:537, and others (U.S. Pat. Nos. 4,474,893, 6,106,833), and chemical coupling of antibody fragments (Brennan et al, 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immnol. 148: 1547) or other lock and key interactive domain structures as described in U.S. Pat. No. 5,582,996. Additional useful techniques include those described in Kortt et al., 1997, supra; U.S. Pat. Nos. 5,959,083; and 5,807,706.

Antibodies according to the invention will typically have a $K_d$ in the range of $10^{-7}$ to $10^{-13}$M; in some preferred embodiments the antibodies have a $K_d$ of less than $10^{-9}$ M. In one embodiment, the antibodies of the invention specifically bind to the disclosed fusion proteins with higher affinity than they bind to other targets, including to the individual fusion partners IL17RC, CRELD1, SCNN1A, TNFRSFIA, CTSD and IFITM10. In some preferred embodiments the antibodies bind the fusion polypeptides with at least 10-fold higher affinity than they bind any of the individual fusion partners; in some preferred embodiments the antibodies bind the fusion polypeptides with at least 100-fold higher affinity than they bind any of the fusion partners.

In some embodiments of the invention a bispecific binding agent, e.g., a bispecific antibody, recognizes the fusion proteins, with one antigen-binding site recognizing SCNN1A and another antigen-binding site recognizing TNFRSF1 A. In some embodiments one antigen-binding site recognizes the fusion protein and another antigen-binding site recognizes another antigen such as, e.g., an antigen expressed on a T-cell in order to leverage the cytotoxicity of T cells. In some embodiments the bispecific antibodies have a lower affinity, e.g., a $K_d$ of greater than 100 nM for each arm, in order to take advantage of the avidity enhancement that can result from bispecific binding.

Methods of Diagnosis

Figure 2:
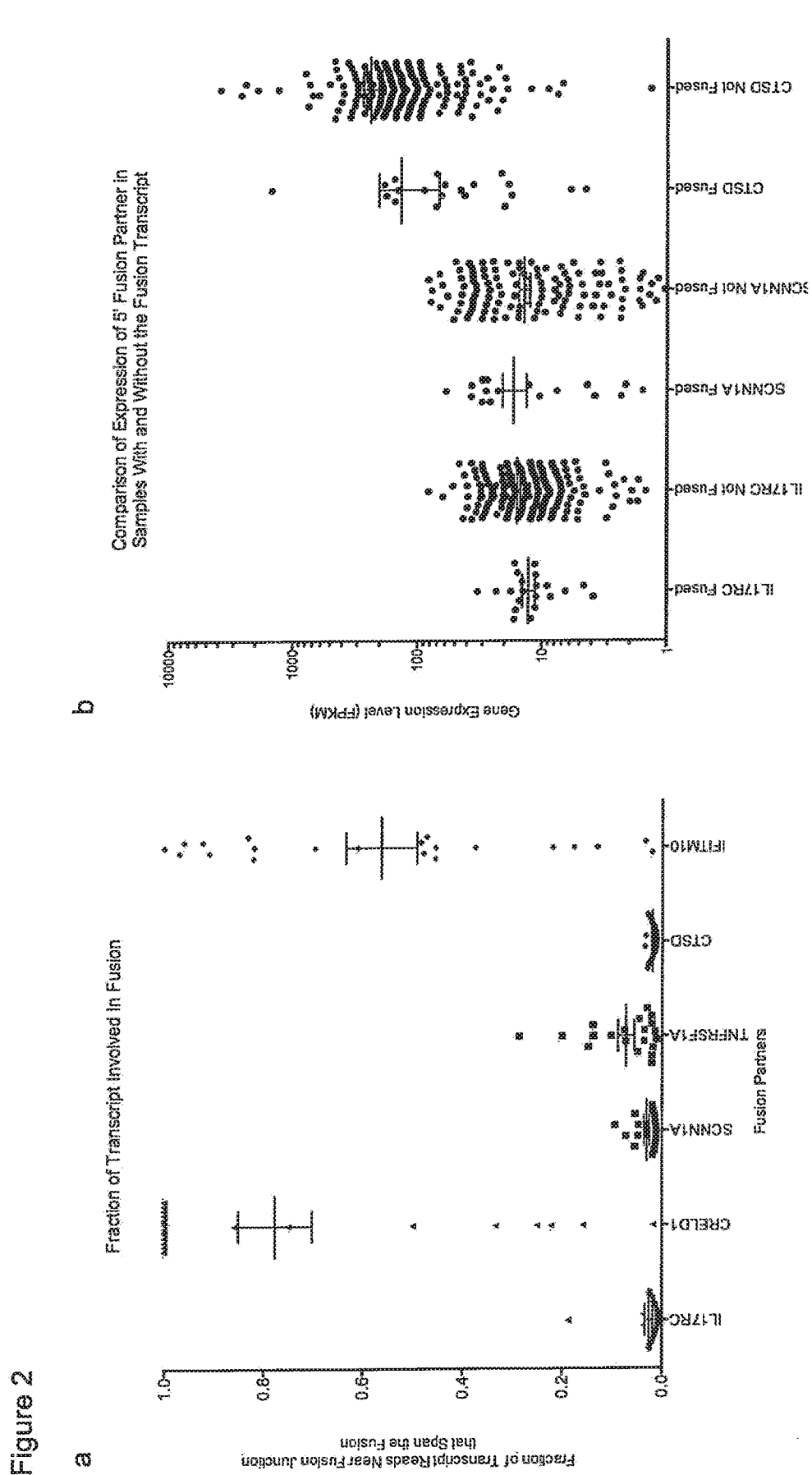
FIG. 2 shows the expression of fusion partners for breast cancer associated read-through fusion transcripts. a) The fraction of reads near the fusion junction that include sequence from the fusion transcript rather than the un-fused canonical transcript was computed. Mean and standard error of the mean are shown. Less than 20%/o of the 5' fusion partners' transcripts have the fusion sequence, indicating that most of the transcripts from the 5' fusion partners are not fused. A significantly larger fraction of the 3' fusion partners' transcripts contain the fusion sequence. Without being limited to this theory, Applicants believe this indicates that the expression of the 3' fusion partner is composed of a large fraction of fusion transcript driven by the 5' fusion partner's promoter. b) There is no difference in the expression levels (Fragments Per Kilobase of transcript Per Million reads; FPKMs) of the 5' fusion partner between samples with or without the read-through fusion transcript (labeled Fused and Not Fused, respectively). Mean and standard error of the mean are depicted in black. Without being limited to this theory, Applicants believe this indicates that increased expression of the 5' fusion partner is not sufficient to induce read-through fusion transcripts, and that lower expression of the 5' partner is not associated with our power to detect the read-through fusion transcripts.
Figure 3:
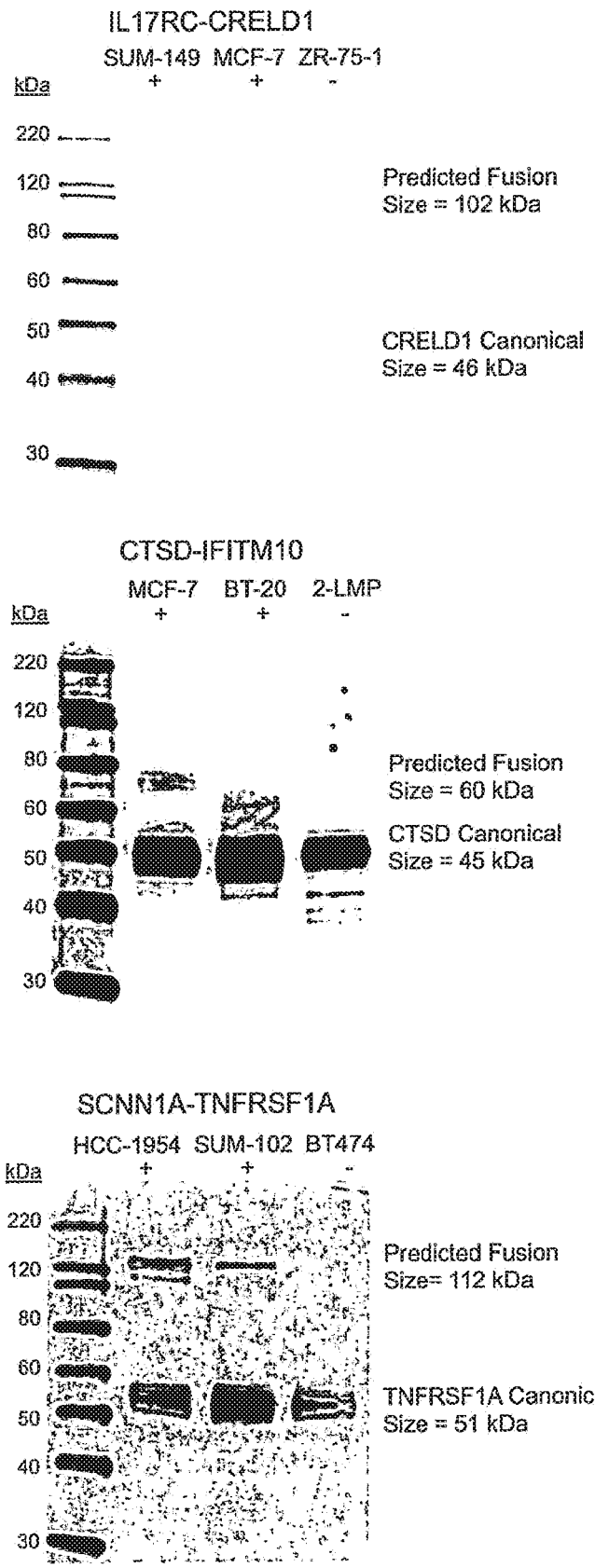
FIG. 3 shows western blots of three breast cancer associated fusion proteins. Western blots were performed using antibodies raised to one of the fusion partner proteins for the three breast cancer associated fusion transcripts. For each candidate fusion, cell lysates from two cell lines were analyzed with RNA-seq reads spanning the fusion junction and one cell line without RNA-seq reads spanning the fusion junction. In each blot, the canonical/native size of the targeted protein was detected in each cell line, and a band at the predicted fusion protein size was detected in the cell line with the most RNA-seq fusion-spanning reads (IL17RC-CRELD1 in SUM-149, CTSD-IFITM10 in MCF7, and SCNN1A-TNFRSF1A in HCC1954). A band corresponding to the size of the predicted fusion protein was also detected in the cell line with the second most RNA-seq fusion transcript reads for the SCNN1A-TNFRSF1A (SUM-102). None of the cell lines without RNA-seq evidence of the fusion transcript produced fusion protein-sized bands.

As illustrated in FIGS. 1-3, the fusion transcripts and the resulting fusion polypeptides described herein are expressed in certain tumors, including breast tumors. In one embodiment, such fusion transcripts and fusion polypeptides are expressed in breast cancer. In one embodiment, such fusion transcripts and fusion polypeptides exhibit differentially increased expression in breast cancer and as compared to normal breast cells and other neoplastic tissue. In one embodiment, such fusion transcripts and fusion polypeptides exhibit differentially increased expression in human breast cancer as compared to normal human breast cells and other human neoplastic tissue. In one embodiment, such fusion transcripts and fusion polypeptides exhibit differentially increased expression in estrogen receptor positive (ER+) breast cancer primary tumors and triple negative breast cancer (TNBC) primary tumors as compared to normal breast cells and other neoplastic tissue. In one embodiment, such fusion transcripts are significantly associated with human breast cancer; in one such embodiment, the human breast cancer is ER+ breast cancer or TNBC.

RNA-seq (35) was performed on a total of 168 human samples, including 28 breast cancer cell lines, 42 fresh frozen triple negative breast cancer (TNBC) primary tumors, 42 fresh frozen estrogen receptor positive (ER+) breast cancer primary tumors, 21 fresh frozen non-neoplastic breast tissue samples that were adjacent to TNBC tumors, 30 fresh frozen non-neoplastic breast tissue samples that were adjacent to ER+ breast tumors, and 5 fresh frozen normal breast tissue samples that were collected from cancer-free patients during reduction mammoplasty procedures. RNA-seq data from 13 non-neoplastic human tissues collected by the Illumina Body Map 2.0 project was obtained, which includes adipose, brain, breast, colon, heart, kidney, liver ovary, prostate, skeletal muscle, testes, thyroid and white blood cells (15). The ChimeraScan software package was used to identify read-through transcripts in the RNA-seq data (36).

With these methods, 17 candidate read-through fusion transcripts were identified that were supported by at least 10 read-pairs that connect adjacent genes and at least one read that spanned the fusion junction in more than two breast cancer samples. Six fusion polypeptides were also detected in one or more non-neoplastic tissues from the Illumina Human Body Map 2.0 project and three transcripts were assigned to pairs of putative transcripts whose boundaries are not well defined. The remaining eight transcripts are breast tissue-specific read-through fusion transcripts. Read-through fusion transcripts with fusion junction-spanning reads are depicted in FIG. 1, and the number of fusion junction-spanning reads in each sample is reported in Supplemental Table 1.

For each of the eight fusion transcripts, it was determined how many samples had at least one fusion junction-spanning read out of a collection of breast cancer cell lines, TNBC primary tumors, ER+ primary tumors, normal uninvolved tissue adjacent to each primary tumor type, and cancer-free normal tissue from reduction mammoplasty procedures (Table 1). Table 1 characterizes the read-through fusion transcripts detected in breast cell line and breast tissue samples. For each fusion transcript the number of samples containing junction-spanning reads is listed. Read-through fusion transcripts significantly associated with breast cancer are IL17RC/CRELD1, SCNN1A/TNFRSF1A and CTSD/IFITM10 and p-values are listed in the last column. * More prevalent in non-cancer samples.

To determine which read-through fusion transcripts were associated with breast cancer Fisher's Exact test was used to identify fusions that were significantly overrepresented in the breast cancer samples compared to the non-cancer breast samples (Table 1). Five of the read-through fusion transcripts were found at high frequency in normal breast tissue and were not significantly associated with breast cancer (KLF16-REXO1, VAX2-ATP6V1B1, LOC100132832-CCDC146, MFGE8-HAPLN3, and CACNG4-CACNG1; Table 1).

| Fusion Transcripts | Breast Cancer Cell Lines (N = 28) | TNBC Primary Tumors (N = 42) | ER+ Breast Cancer Primary Tumors (N = 42) | Normal Uninvolved Tissue Adjacent to TNBC (N = 2.1) | Normal Uninvolved Tissue Adjacent to ER+ Breast Cancer (N = 30) | Cancer-Free Reduction Mammoplasty Breast Tissue (N = 5) | Human Body Map (N = 13) | Cancer vs. Normal Fisher's Exact Test p-value |
|---|---|---|---|---|---|---|---|---|
| KLF16-REXO1 | 7 (25%) | 18 (43%) | 16 (38%) | 14 (67%) | 15 (50%) | 2 (40%) | 0 (0%) | 0.1699* |
| VAX2-ATP6V1B1 | 6 (21%) | 8 (19%) | 4 (10%) | 4 (19%) | 3 (10%) | 2 (40%) | 0 (0%) | 0.3711 |

-continued

| Fusion Transcripts | Breast Cancer Cell Lines (N = 28) | TNBC Primary Tumors (N = 42) | ER+ Breast Cancer Primary Tumors (N = 42) | Normal Uninvolved Tissue Adjacent to TNBC (N = 2.1) | Normal Uninvolved Tissue Adjacent to ER+ Breast Cancer (N = 30) | Cancer-Free Reduction Mammoplasty Breast Tissue (N = 5) | Human Body Map (N = 13) | Cancer vs. Normal Fisher's Exact Test p-value |
|---|---|---|---|---|---|---|---|---|
| LOC100132832-CCDC146 | 2 (7%) | 11 (26%) | 5 (12%) | 5 (24%) | 3 (10%) | 1 (20%) | 0 (0%) | 0.3711 |
| MFGE8-HAPLN3 | 4 (14%) | 23 (55%) | 4 (10%) | 4 (19%) | 7 (23%) | 1 (20%) | 0 (0%) | 0.0794 |
| CACNG4-CACNG1 | 2 (7%) | 2 (5%) | 12 (29%) | 1 (5%) | 3 (10%) | 0 (0%) | 0 (0%) | 0.0600 |
| IL17RC-CRELD1 | 3 (11%) | 11 (26%) | 4 (10%) | 3 (14%) | 1 (3%) | 0 (0%) | 0 (0%) | 0.0306 |
| SCNN1A-TNFRSF1A | 10 (36%) | 3 (7%) | 5 (12%) | 1 (5%) | 1 (3%) | 0 (0%) | 0 (0%) | 0.0039 |
| CTSD-IFITM10 | 7 (25%) | 9 (21%) | 5 (12%) | 0 (0%) | 0 (0%) | 0 (0%) | 0 (0%) | <0.0001 |

Three read-through fusion transcripts were significantly associated with breast cancer (IL17RC-CRELD1, SCNN1A-TNFRSF1A and CTSD-IFITM10; Fisher's Exact Test p-values in Table 1). Two of these breast-cancer associated fusion transcripts were detected across breast tumors but were also detected at a lower frequency in normal uninvolved tissue that was adjacent to the primary tumors (IL17RC-CRELD1, and SCNN1A-TNFRSF1A) (Table 1). The breast tumors underwent macro-dissection to enrich for tumor cells; however the adjacent normal uninvolved tissue was not dissected. Pathologists used a quality control section to diagnose the uninvolved tissue, but the specimen could have had infiltrating tumor cells or tumor exosomes containing mRNA deeper within the specimen. Neither of these fusions was detected in the cancer-free normal breast tissues from reduction mammoplasty procedures, suggesting that the low frequency of these fusions in the normal uninvolved tissue adjacent to tumors could be due to field defects. One fusion transcript, CTSD-IFITM10, was identified exclusively in breast cancer samples. All three of the breast cancer associated fusions were present in both ER+ and TNBC, and while they are present in different frequencies between the breast cancer subtypes, none are exclusive to a particular subtype. One or more of the breast cancer associated read-through fusion transcript were detected in 50% (14/28) of the breast cancer cell lines, 43% (18/42) of the TNBC primary tumors, and 24% (10/42) of the ER+ breast cancer primary tumors demonstrating that these are frequent events in breast cancer.

All three of the breast cancer associated read-through fusion transcripts are spliced together using the last splice donor from the 5' fusion partner and the first splice acceptor in the 3' gene partner, skipping the last exon of the 5' fusion partner and the first exon of the 3' gene partner (FIG. 1). For example, CTSD has nine (9) exons and IFITM10 has three (3) exons, so the CTSD/IFITM10 fusion protein is spliced at the eighth ($8^{th}$) exon of CTSD and the second ($2^{nd}$) exon of IFITM10.

In each case, this results in splicing together nearly the full-length transcripts for both genes. Normally the 5' fusion partner's transcript should be terminated by cleavage of the nascent transcript followed by polyadenylation (37). These read-through fusion transcripts have not been cleaved at the 5' partner gene's polyA signal and the 5' partner gene's terminal exon splice acceptor site has been skipped to allow splicing between the adjacent genes. It is increasingly evident that the processes of transcription, splicing, 3' transcript cleavage, and polyadenylation are coupled (38).

One possible explanation for the generation of read-through fusion transcripts is that the 5' partner gene's terminal exon was skipped because of a mutation at the splice acceptor site, which could hinder formation of the 3'-terminal exon-definition complex and subsequent cleavage/polyadenylation. If this were to occur, then the next available splice acceptor site would be at the 3' partner gene's $2^{nd}$ exon, consistent with the observed splice junctions. To test this possibility, 200 bp surrounding the 5' fusion partner gene's skipped splice acceptor site were amplified from DNA of cell lines with and without the fusion transcripts and sequenced the amplicons on an Illumina MiSeq machine. No mutations at or near the splice acceptor sites were found associated with the presence of the fusion transcripts. Both alleles of heterozygous SNPs occur at expected frequencies, so deletion of the splice sites is also unlikely. Because the processes of transcription, splicing, 3' transcript cleavage, and polyadenylation can act both synergistically and competitively (38), it is possible that the kinetics of transcription at these loci is disrupted in breast cancer cells in a way that allows the formation of read-through fusion transcripts.

To determine if the expression level of each fusion partner gene was correlated with the presence of the fusion, the sequencing read depth for the canonical transcripts and fusion transcripts was quantified. In each of the samples containing fusion junction-spanning reads, the fraction of reads near the fusion junction that include sequence from the fusion transcript rather than the un-fused canonical transcripts was calculated (FIG. 2a). In each case, the fraction of reads from the 3' fusion partner that is involved in the fusion is significantly higher than the fraction of reads from the 5' partner that is participating in the fusion (Mann Whitney test: IL17RC vs CRELD1 $p<0.0001$, SCNN1A vs TNFRSF1A $p=0.0247$, and CTSD vs IFITM10 $p<0.0001$). This indicates that a larger proportion of the transcription of the 3' partner is created from read-through transcripts, and the promoter of the 5' fusion partner likely regulates this expression. The expression of the 5' fusion partner in samples with and without evidence of the fusion transcript was examined and it was discovered that there was no difference in expression levels of IL17RC, SCNN1A or TNFRSF1A between samples with and without the fusion, indicating that the expression level of the 5' gene partner is not associated with the presence of these fusions nor was the expression level of the 5' gene partner associated with our power to detect the fusion (FIG. 2b). Because the presence of the fusion transcripts is independent of the expression level of the partner genes, this suggests that other factors are responsible for their creation and regulation.

All three of the breast cancer-associated read-through fusion transcripts we identified involved genes that encode membrane proteins. These proteins' functions rely on their correct placement in the membrane and correct participation in protein complexes. IL I17RC is a single-pass type I membrane protein that binds the proinflammatory cytokines, IL-17A and IL-17F (39). It is fused to CRELD1, a membrane protein that contains an epidermal growth factor-like domain and is thought to function as a cell adhesion molecule (40). SCNN1A is an alpha subunit of nonvoltage-gated, amiloride-sensitive, sodium channels (41). It is fused to TNFRSF1A, a tumor necrosis factor-alpha receptor that activates NF-kappaB, mediates apoptosis, and regulates inflammatory responses (42). CTSD is a lysosomal aspartyl protease that also functions as a secreted protein that binds membrane receptors and has previously been associated with breast cancer (43). It is fused to IFITM10, a member of a family of membrane proteins that are induced by interferon and are involved in cell proliferation and cell adhesion (44). All of these read-through fusion transcripts join genes that have disparate functions, suggesting that a fused protein could impair normal function in breast cancer.

The length of the fusion protein based upon the location of the inter-gene splicing, was predicted and Western blots were used with an antibody raised against one of the native partner proteins to determine whether a protein of the predicted fusion size could be detected in cell lysates from cell lines with and without RNA transcript evidence of the fusion. Specific Western blots of the targeted protein at the expected canonical size and detected protein at the predicted fusion size specifically in the cell lines with the fusion transcripts were observed, and not in cell lines without the fusions for all three of the breast cancer associated read-through fusion transcripts (FIG. 3). The cell line with the most fusion-spanning reads was positive for the fusion in all three Western blots, and in the case of the SCNN1A-TNFRSF1A, the cell line with the second highest number of fusion-spanning reads, was also positive by Western blot. These results suggest that the breast-cancer associated read-through fusion transcripts are translated into fusion proteins.

Detecting expression and/or expression levels of the fusion proteins in tissue samples can therefore be used to identify a tumor, characterize a tumor, or to monitor the effects of treatment on tumors that express the identified fusion proteins. In some embodiments expression is detected at the RNA level, using methods described herein and known in the art such as Quantitative PCR, hybridization, in situ hybridization, nanostring technology (such as that described in U.S. Pat. No. 7,473,767), and nucleic acid sequencing. In some embodiments, expression is detected at the protein level, using methods described herein and known in the art such as immunoprecipitation, immunohistochemistry (IHC), Western blot analysis, flow cytometry, ELISA, immunoassays with antibody detection, and mass spectrometry.

Pharmaceutical Compositions, Modes of Administration and Methods of Treatment

The present disclosure provides methods for the treatment and/or prevention of a disease state that is characterized, at least in part, by the expression of an IL17RC-CRELD1, SCNN1A-TNFRSF1A or CTSD-IFITM10 fusion polypeptide. In one embodiment, the disease state is characterized, at least in part, by the differentially increased expression of an IL17RC-CRELD1, SCNN1A-TNFRSF1A or CTSD-IFITM10 fusion transcript or fusion polypeptide. In one embodiment, such a fusion transcript has the sequence of SEQ ID NOS: 1, 2, 3, 8, 11 or 12 or fragments or variants thereof. In one embodiment, such a fusion transcript has the sequence of SEQ ID NOS: 4, 5, 6, 7, 9, 11, 13 or 14 or fragments or variants thereof.

In one embodiment, such fusion transcripts and fusion polypeptides are expressed in a patient suffering from breast cancer. In one embodiment, such fusion transcripts and fusion polypeptides exhibit differentially increased expression in breast cancer and as compared to normal breast cells and other neoplastic tissue. In one embodiment, such fusion transcripts and fusion polypeptides exhibit differentially increased expression in human breast cancer as compared to normal human breast cells and other human neoplastic tissue. In one embodiment, such fusion transcripts and fusion polypeptides exhibit differentially increased expression in estrogen receptor positive (ER+) breast cancer and/or triple negative breast cancer (TNBC) as compared to normal breast cells and other neoplastic tissue. In one embodiment, such fusion transcripts are significantly associated with human breast cancer; in one such embodiment, the human breast cancer is ER+ breast cancer or TNBC. In one embodiment, the disease state is a cancer, such as but not limited to breast cancer. In one embodiment, the breast cancer ER+ breast cancer of TNBC.

The present disclosure provides for compounds that may be used in the methods of treatment and prevention described herein. The compound used in the treatment and/or prevention may be provided alone or as a part of a pharmaceutical composition comprising a pharmaceutically acceptable carrier and other ingredients known in the art. The pharmaceutically acceptable carriers described herein, include, but are not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

In one embodiment, the method of treatment and/or prevention comprises contacting a cell of a subject with an antigen binding agent of the present disclosure. In one embodiment, the method of treatment and/or prevention comprises administering to a subject an antigen binding agent of the present disclosure. In such embodiments, the antigen binding agent is an antibody, such as, but not limited to, a monoclonal antibody or a polyclonal antibody. Bispecific antibodies are included therein. In such embodiment, the antigen binding agent may be provided in a therapeutically effective amount. In such embodiment, the methods may further comprise identifying a subject in need of such treatment or prevention. In one embodiment of the foregoing, such a subject may be screened to determine the presence of a fusion transcript or fusion polypeptide of the present disclosure. Further such subject may be screened to determine if the subject has ER+ breast cancer or TNBC.

The compounds and pharmaceutical compositions can be administered by any conventional method available for use in conjunction with pharmaceuticals, either individually or in combination with additional therapeutic agents. In one embodiment, the compounds and pharmaceutical compositions are administered in therapeutically effective amount. The therapeutically effective amount and the dosage of the compound or pharmaceutical composition administered will, of course, vary depending upon known factors, such as the pharmacodynamic characteristics; the mode and route of administration, the age, health and weight of the subject; the severity and stage of the disease state; the kind of concurrent treatment; the frequency of treatment; and the effect desired. The total amount of the compound (i.e. active ingredient) administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

A daily dosage of active ingredient can be expected to be about 0.001 to 1000 milligrams (mg) per kilogram (kg) of body weight. In one embodiment, the total amount is between about 0.1 mg/kg and about 1000 mg/kg of body weight; in an alternate embodiment between about 1.1 mg/kg and about 100 mg/kg of body weight; in yet another alternate embodiment between 0.1 mg/kg and about 30 mg/kg of body weight. The above described amounts may be administered as a series of smaller doses over a period of time if desired. As would be obvious, the dosage of active ingredient may be given other than daily if desired.

Dosage forms of the pharmaceutical compositions described herein (forms of the pharmaceutical compositions suitable for administration) may contain from about 0.1 mg to about 500 mg of active ingredient per unit. In these pharmaceutical compositions, the active ingredient will ordinarily be present in an amount of about 0.5-95% weight based on the total weight of the composition. Multiple dosage forms may be administered as part of a single treatment.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation via the pulmonary system, such as by propellant based metered dose inhalers or dry powders inhalation devices. Other dosage forms are potentially possible such as administration transdermally, via patch mechanisms or ointment.

Formulations suitable for oral administration can consist of (a) liquid solutions, such as a pharmaceutically effective amount of the compound dissolved in diluents, such as water, saline, or orange juice; (b) capsules, sachets, tablets, lozenges, and troches, each containing a predetermined pharmaceutically effective amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Forms of systemic administration of the pharmaceutical compositions include injection and infusion. Such injection and infusion routes, include, but are not limited to, subcutaneous, intramuscular, intracranial and intraperitoneal.

Alternative means for systemic administration include transmucosal and transdermal administration using penetrants such as bile salts or fusidic acids or other detergents.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbents and diluents, surface active agents, suspending agent, tableting binders, lubricants, flavors, and coloring agents.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include pastilles comprising the active ingredient in an inert base, such as gelatin and glycerin, or sucrose and acacia, as well as creams, emulsions, and gels containing, in addition to the active ingredient, such carriers as are known in the art. Furthermore, transdermal patches can be prepared using methods known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an patient are available, and, although more than one route can be used to administer a particular compound, a particular route can provide a more immediate and more effective reaction than another route.

In one embodiment, the compound used in the treatment of the disease state is an antibody or other antigen binding agent. The antibodies or other antigen binding agents of the invention may be used to inhibit proliferation of cells that exhibit differentially increased expressions of the fusion proteins and polypeptides disclosed herein.

In certain embodiments, the antibodies or other antigen binding agents are administered alone. In certain embodiments, the antibodies or other antigen binding agents are administered prior to the administration of at least one other therapeutic agent. In certain embodiments, the antibodies or other antigen binding agents are administered concurrent with the administration of at least one other therapeutic agent. In certain embodiments, the antibodies or other antigen binding agents are administered subsequent to the administration of at least one other therapeutic agent. Exemplary therapeutic agents include, but are not limited to, radiation therapy and chemotherapy. Such co-administration may improve the effectiveness of the compounds and pharmaceutical compositions and the methods of treatment and prevention disclosed herein. Furthermore, such co-administration of the compounds and pharmaceutical compositions disclosed herein may improve the effectiveness of the known breast cancer therapies.

In some embodiments of the invention the antibodies or other antigen binding agents are able to directly bind to a fusion polypeptide of the present disclosure and/or modulate the function of the fusion polypeptide of the present disclosure and therefore selectively kill tumor cells expressing such fusion polypeptides.

In some embodiments of the invention, the cell killing ability of an antigen binding agent, such as, but not limited, an antibody, is improved through conjugation to a cytotoxic agent or by enhancing an antibody effector function. These embodiments are particularly well-suited to killing cancer cells that express the fusion polypeptides of the present disclosure. Antibodies with improved cell-killing ability, such as antibodies conjugated to a cytotoxic agent or antibodies with enhanced effector function, can be used to kill tumor cells expressing the fusion polypeptides whether or not those fusion polypeptides are functional and whether or not the antibodies modulate that function. This is an important therapeutic advantage in the treatment of tumors.

The invention therefore includes compositions and use of antigen binding agent-drug conjugates, or "ADCs" (which are also referred to immunoconjugates) comprising an antigen binding agents, such as, but not limited to, an antibody, conjugated to a cystostatic agent and/or a cytotoxic agent such as, but not limited to, a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate). The use of immunoconjugates for the local delivery of cytotoxic or cytostatic agents to kill or inhibit the proliferation of tumor cells in the treatment of cancer (Lambert, J., 2005, Curr. Opinion in Pharmacology 5:543-549; Wu et al, 2005, Nature Biotechnology 23(9): 1 137-L146; Payne, G., 2003, Cancer Cell 3:207-212; Syrigos and Epenetos, 1999, Anticancer Research 19:605-614; Nicutescu-Duvaz and Springer, 1997, Adv. Drug Del. Rev. 26: 151-172; U.S. Pat. No. 4,975,278) allows targeted delivery of the such agents to tumors, and intracellular accumulation therein, where systemic administration of these unconjugated agents may result in unacceptable levels of toxicity to normal cells as well as the tumor cells sought to be eliminated (Baldwin et al, 1986, Lancet pp: 603-05; Thorpe, 1985 "Antibody Carriers Of Cytotoxic Agents In Cancer Therapy: A Review," in Monoclonal Antibodies '84: Biological And Clinical Applications, A. Pinchera et al (ed.s), pp. 475-506). Efforts to improve the therapeutic index (i.e. maximal efficacy and minimal toxicity of Immunoconjugates) have focused on the selectivity of polyclonal (Rowland et al, 1986, Cancer Immunol. Immunother., 21:183-87)

and monoclonal antibodies (mAbs) as well as drug-linking and drug-releasing properties (Lambert, J., 2005, Curr. Opinion in Pharmacology 5:543-549). Agents used in such immunoconjugates conjugates include bacterial protein toxins, such as, but not limited to, diphtheria toxin, plant protein toxins such as, but not limited to, ricin and saporin, small molecules, such as, but not limited to, auristatins, geldanamycin (Mandler et al., 2000, J. of the Nat. Cancer Inst. 92(19): 1573-1581; Mandler et al., 2000, Bioorganic & amp; Med. Chem. Letters 10: 1025-1028; Mandler et al., 2002, Bioconjugate Chem. 13:786-791), maytansinoids (EP 1391213; Liu et al., 1996, Proc. Natl. Acad. Sci. USA 93:8618-8623), calicheamicin (Lode et al., 1998, Cancer Res. 58:2928; Hinman et al., 1993, Cancer Res. 53:3336-3342), daunomycin, doxorubicin, methotrexate, and vindesine.

In some embodiments of the invention the antigen binding agents, such as, but not limited to, antibodies, have an enhanced effector function. An "effector function" refers to those biological activities attributable to the Fc region of an antibody, including complement-dependent cytotoxicity (CDC) and antibody-dependent cell-mediated cytotoxicity (ADCC). ADCC is a cell-mediated reaction in which non-specific cytotoxic cells that express Fc receptors recognize bound antibody on a target cell and subsequently cause lysis of the target cell. In some embodiments, the ADCC activity has been enhanced through methods known in the art such as modification of the Fc sequence or modification of the carbohydrate structure, e.g., reducing fucose in the Fc-linked oligosaccharide structure of the antibodies to create "afucosylated antibodies."

In one embodiment, the composition administered to a patient is a siRNA construct as discussed below.

RNAi

RNAi is the process of sequence-specific post transcriptional gene silencing mediated by siRNA. Long double stranded RNA (dsRNA) in cells stimulates the activity of a ribonuclease III enzyme referred to as dicer. Dicer is involved in the processing of the long dsRNA into short pieces of siRNA. siRNAs derived from dicer activity are typically about 21-23 nucleotides in length and include duplexes of about 19 base pairs.

The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex. siRNA mediated RNAi has been studied in a variety of systems. Recent work in Drosophila embryonic lysates has revealed certain requirements for siRNA length, structure, chemical composition, and sequence that are essential to mediate efficient RNAi activity. RNAi technology has been used in mammalian cell culture, where a siRNA-mediated reduction in gene expression has been accomplished by transfecting cells with synthetic RNA oligonucleotides. The ability to use siRNA-mediated gene silencing in mammalian cells combined with the high degree of sequence specificity allows RNAi technology to be used to selectively silence expression of mutant alleles or toxic gene products in dominantly inherited diseases, including neurodegenerative diseases. Several neurodegenerative diseases, such as Parkinson's disease, Alzheimer's disease, Huntington's disease, Spinocerebellar Ataxia Type 1, Type 2, and Type 3, and dentatorubral pallidoluysian atrophy (DRLPA), have proteins identified that are involved in the overall pathogenic progression of the disease.

Figure 4:
FIG. 4 shows the results of investigating the CTSD-IFITM10 and SCNN1A-TNFRSF1A expression in vitro. a) For each fusion transcript we designed qPCR primer to flank the fusion junctions and we designed two custom siRNAs to target the fusion junction. The sequence from the 5' gene is indicated in green and the sequence from the 3' gene is indicated in red. b) The CTSD-IFITM10 fusion transcript was detected in RNA-seq data from the MCF7 breast cancer cell line, and the SCNN1A-TNFRSF1A fusion transcript was detected in RNA-seq data from the HCC1954 breast cancer cell line. To confirm the presence of each fusion in these cell lines we performed qPCR on cDNA and electrophoresed the products in a 4% agarose gel. PCR products of the expected size were amplified from cDNA using primers that flank the fusion junction between the two genes, and there were no products generated in the PCR reaction that did not contain cDNA, confirming the presence of these fusion transcripts in each cell line. c) The MCF7 breast cancer cell line was transfected with two siRNAs targeting the CTSD-IFITM10 fusion junction. QPCR of the fusion transcript was performed 48 hours after transfection. Both siRNAs significantly reduced the abundance of the fusion transcript relative to the controls, which included a non-targeting siRNA and a mock transfection that did not contain any siRNA. d) The HC1954 breast cancer cell line was transfected with two siRNAs targeting the SCNN1A-TNFRSF1A fusion junction. QPCR of the fusion transcript was performed 48 hours after transfection. One siRNA, represented by SEQ ID. NOS. 19 and 20, significantly reduced the abundance of the fusion transcript relative to the controls, which included a non-targeting siRNA and a mock transfection that did not contain any siRNA. e) The MCF7 breast cancer cell line was transfected with two siRNAs targeting the CTSD-IFITM10 fusion junction. A quantitative cell proliferation assay was performed 72 hours after transfection. Both siRNA constructs, represented by SEQ ID NOS. 15 and 16, and 17 and 18, respectively significantly reduced the number of live cells relative to the controls, indicating that the CTSD-IFITM10 fusion transcript is associated with proliferation in this breast cancer cell line.
Figure 4:
Figure 4:
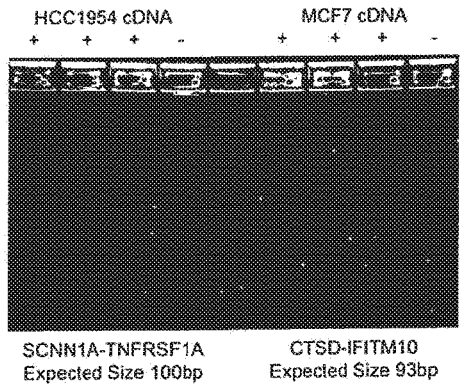
Figure 4:
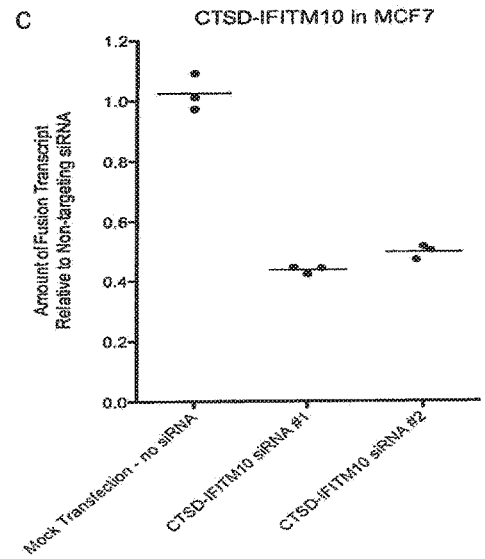
Figure 4:
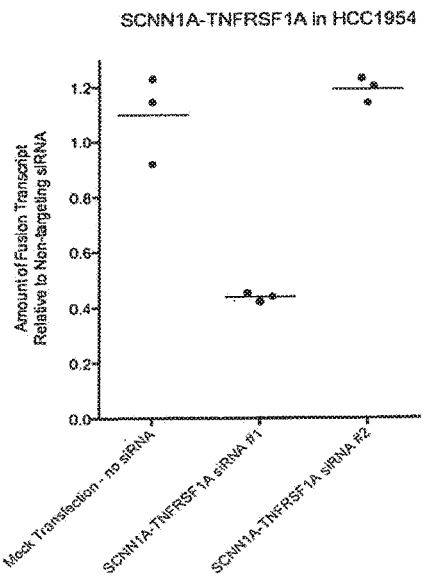
Figure 4:
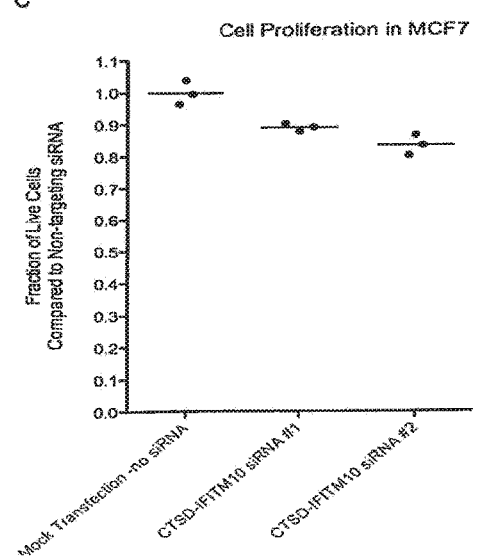

In one embodiment, the present invention relates to the use of a siRNA construct to silence the expression of, or down regulate the expression of, a IL17RC-CRELD1, SCNN1A-TNFRSF1A and CTSD-IFITM10 fusion polypeptide or a gene expressing the IL17RC-CRELD1, SCNN1A-TNFRSF1A and CTSD-IFITM10 fusion polypeptide. In another aspect, the invention relates to the use of a siRNA construct that is targeted to the IL17RC-CRELD1, SCNN1A-TNFRSF1A or CTSD-IFITM10 fusion polypeptide/nucleotide in the treatment of cancer, such as breast cancer. According to still another aspect of the present invention is a method for increasing the efficacy of cancer therapy in a subject, the method comprising: administering to a subject in need of an effective amount of an siRNA construct directed to the IL17RC-CRELD1, SCNN1A-TNFRSF1A and CTSD-IFITM10 fusion polypeptide, wherein said subject is also being administered a cancer therapy selected from the group consisting of small-molecule drugs, angiogenesis inhibitors, tumor vaccine, chemotherapy, immunotherapy, radiation therapy, gene therapy and combinations thereof. As shown in FIG. 4, the siRNA constructs disclosed herein effectively silence, or downregulates, the expression of the SCNN1A-TNFRSF1A or CTSD-IFITM10 fusion polypeptides.

The CTSD-IFITM10 fusion transcript was detected in RNA-seq data from the MCF7 breast cancer cell line and the SCNN1A-TNFRSF1A fusion transcript was detected in RNA-seq data from the HCC1954 breast cancer cell line, which makes them amenable to further investigation in vitro. qPCR primers were designed flanking the fusion junction for each transcript (FIG. 4a). We prepared cDNA from each of the cell lines and performed qPCR using the junction flanking primers. The qPCR successfully amplified a product from cDNA from each cell line, and the product was the expected size when electrophoresed on a 4% agarose gel (FIG. 4b). The negative control, which contained all reaction components except cDNA, did not produce a qPCR product (FIG. 4b). Together these results confirm the presence of the fusion transcript detected by RNA-seq in each cell line. The qPCR primers identified herein (SEG ID NOS.: 23-26) are capable of identifying the fusion transcripts.

Two siRNA duplexes to target the fusion junction of each fusion transcript were designed as shown in FIG. 4a, wherein CTSD-IFITM10 siRNA #1 corresponds to SEQ ID NOS.: 15 (sense) and 16 (anti-sense), CTSD-IFITM10 siRNA #2 corresponds to SEQ ID NOS.: 17(sense) and 18 (anti-sense). Further, in FIG. 4a, SCNN1A-TNFRSF1A siRNA #1 corresponds to SEQ ID NOS.: 19(sense) and 20(anti-sense) SCNN1A-TNFRSF1A siRNA #2 corresponds to SEQ ID NOS.: 21(sense)-22(anti-sense). We transfected the cell lines with the siRNA duplexes targeting the fusion transcript and measured the abundance of fusion transcript 48 hours after transfection using the qPCR primers flanking the fusion junction. In FIG. 4a, the CTSD-IFITM10 qPCR forward primer corresponds to SEQ ID. NO. 23 and the CTSD-IFITM10 qPCR reverse primer corresponds to SEQ ID. NO. 24. Further, the SCNN1A-TNFRSF1A qPCR forward primer corresponds to SEQ ID. NO. 25 and the SCNN1A-TNFRSF1A qPCR reverse primer corresponds to SEQ ID. NO. 26. We measured the fusion transcript abundance in three control samples transfected with a non-targeting siRNA and in three experiment samples transfected with each of the siRNAs targeted to the fusion junction.

Both siRNA constructs (SEQ ID NOS. 15-18) targeting the fusion junction of the CTSD-IFITM10 fusion transcript produced knockdown of the fusion transcript in the MCF7 cell line resulting in only 42% to 51% of the transcript remaining relative to the cells treated with the non-targeting siRNA, which indicates that the fusion transcript abundance can be reduced with these siRNAs (FIG. 4c). One siRNA construct (SEQ ID NOS. 19 and 20) targeting the fusion junction of the SCNN1A-TNFRSF1A fusion transcript produced knockdown of the fusion transcript in HCC1954 resulting in only 42% to 45% of the transcript remaining relative to the cells treated with the non-targeting siRNA, which indicates that this siRNA can be used to reduce the abundance of the SCNN1A-TNFRSF1A fusion transcript (FIG. 4d).

To determine if knockdown of the fusion transcripts affects cell proliferation we measured the number of live cells 72 hours after transfection with each siRNA targeting the fusion junction. We compared the number of live cells between samples transfected with non-targeting siRNA and those transfected with each of the siRNAs targeting the fusion junctions. We found that the two siRNAs targeting the CTSD-IFITM10 fusion transcript resulted in a significant decrease in the number of live MCF7 cells after 72 hours ($p<0.03$) resulting in 10% to 17% reduction in live cell numbers, indicating that the abundance of this fusion transcript is associated with cell proliferation (FIG. 4e). While this decrease is modest, it is important to note that this cell viability effect is evident even when 45% of the fusion transcript is remaining after knockdown, and could exhibit a more profound effect on proliferation with greater knockdown. The two siRNAs targeting the SCNN1A-TNFRSF1A fusion transcript were not associated with difference in the number of live HCC1954 cells, indicating that the 55-58% knockdown of the fusion transcript was not associated with a cell proliferation differences, but we cannot rule out the possibility that a more dramatic difference in the amount of transcript could reveal an association with cell proliferation. The significant association between the CTSD-IFITM10 fusion transcript abundance and MCF7 cell proliferation indicates that this novel fusion transcript may play a role in breast cancer cell proliferation.

The siRNA of the present invention may be expressed from a recombinant plasmid either as two separate, complementary RNA molecules, or as a single RNA molecule with two complementary regions. Selection of vectors suitable for expressing siRNA of the invention, methods for inserting nucleic acid sequences for expressing the siRNA into the plasmid, and methods of delivering the recombinant plasmid to the cells of interest are within the skill in the art. Methods for constructing recombinant DNA vectors and the production of DNA may be found in Sambrook et al., infra, for example.

The siRNA of the present invention may be a polynucleotide sequence cloned into a plasmid vector and expressed using any suitable promoter. Suitable promoters for expressing siRNA of the invention from a plasmid include, but are not limited to, the H1 and U6 RNA pol III promoter sequences and viral promoters including the viral LTR, adenovirus, SV40, and CMV promoters. Additional promoters known to one of skill in the art may also be used, including tissue specific, inducible or regulatable promoters for expression of the siRNA in a particular tissue or in a particular intracellular environment. The vector may also include additional regulatory or structural elements, including, but not limited to introns, enhancers, and polyadenylation sequences. These elements may be included in the DNA as desired to obtain optimal performance of the siRNA in the cell and may or may not be necessary for the function of the DNA. Optionally, a selectable marker gene or a reporter gene may be included either with the siRNA encoding polynucleotide or as a separate plasmid for delivery to the target cells. Additional elements known to one of skill in the art may also be included.

The siRNA may also be expressed from a polynucleotide sequence cloned into a viral vector that may include the elements described above. Suitable viral vectors for gene delivery to a cell include, but are not limited to, replication-deficient viruses that are capable of directing synthesis of all virion proteins, but are incapable of making infections particles. Exemplary viruses include, but are not limited to lentiviruses, adenoviruses, adeno-associated viruses, retroviruses, and alphaviruses.

Adenovirus, AAV, and lentiviral vectors may be used for gene delivery to the nervous system, including the central nervous system and the peripheral nervous system, where cell division is limited, to infect terminally differentiated cells without the need for cell division. (Davidson et al., Nat. Genet. 3:219-223, 1993; Mastrangeli et al., Clin. Res. 41:223A (Abstract), 1993; Ghadge et al., Gene Ther. 2:132-137, 1995; Xiao et al., Exp. Neurol. 144:113-124, 1997; McCown et al., Brain Res. 713:99-107, 1996; Davidson and Bohn, Exp. Neurol. 144(1):125-30, 1997; Choi-Lundberg, D. L. and Bohn, M. C, Stem Cell Biology and Gene Therapy, Quesenberry, P. J., Stein, G. S., Forget, B. and Weissman, S. (Eds), J. Wiley & Sons, New York, pp. 503-553, 1998; Chamberlin et al., Brain Res. 793:169-175, 1998; Blomer et al., J. Virol. 71:6641-6649, 1997; Zufferey et al., Nat. Biotechnol. 15:871-875, 1997; Kordower et al., Exp. Neurol. 160:1-16, 1999). The recombinant lentivirus vectors remain capable of infecting non-dividing cells when deleted of accessory proteins (Johnston et al., J. Virol. 73:4991-5000, 1999, Naldini, Throm. Haemat. 82:552-554, 1999).

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA or RNA duplex into a host cell include, but are not limited to, calcium phosphate precipitation, lipofection, DEAE-dextran, particle bombardment, microinjection, electroporation, immunoliposomes, lipids, cationic lipids, phospholipids, or liposomes and the like. One skilled in the art will understand that any method may be used to deliver the DNA or RNA duplex into the cell.

One mode of administration to the CNS uses a convection-enhanced delivery (CED) system. This method includes: a) creating a pressure gradient during interstitial infusion into white matter to generate increased flow through the brain interstitium (convection-supplementing simple diffusion); b) maintaining the pressure gradient over a lengthy period of time (24 hours to 48 hours) to allow radial penetration of the migrating compounds (such as: neurotrophic factors, antibodies, growth factors, genetic vectors, enzymes, etc.) into the gray matter; and c) increasing drug concentrations by orders of magnitude over systemic levels. Using a CED system, DNA, RNA duplexes or viruses can be delivered to many cells over large areas of the brain. Any CED device may be appropriate for delivery of DNA, RNA or viruses. In some embodiments, the device is an osmotic pump or an infusion pump. Both osmotic and infusion pumps are commercially available from a variety of suppliers, for example Alzet Corporation, Hamilton Corporation, Alza, Inc., Palo Alto, Calif.

Biological methods to introduce the nucleotide of interest into a host cell include the use of DNA and RNA viral vectors. For mammalian gene therapy, it is desirable to use an efficient means of inserting a copy gene into the host genome. Viral vectors have become the most widely used method for inserting genes into mammalian, e.g., human cells.

Delivery of the recombinant nucleotides to the host cell may be confirmed by a variety of assays known to one of skill in the art. Assays include Southern and Northern blotting, RT-PCR, PCR, ELISA, and Western blotting, by way of example.

Infective virus particles will be produced from the viral vectors of the present invention using standard methodology, known to one of skill in the art. The methods generally involve introducing the viral vector containing the siRNA encoding polynucleotide into a producer cell. By way of example, the producer cell for a lentiviral vector generally includes gag/pol and env coding sequences. AAV virus production also includes introducing a helper construct into the producer cell, where the helper construct includes coding regions capable of being expressed in the producer cell to complement helper functions missing from the replication deficient viral vector. For AAV vectors helper functions include, but are not limited to, ORFs, namely the rep and cap coding regions, or functional homologues thereof; and helper functions from herpes virus or adenovirus, such as E1A, E2, E3 and E4. The production of virus particles also includes culturing the producer cell to produce virions. The siRNA expression vector, and if necessary, helper construct(s) for AAV can be introduced into the producer cell, either simultaneously or serially, using standard transfection techniques known to one of skill in the art (Zoltukhin et al., Gene Therapy, 6:973-985, 1999).

The virions are then harvested from the supernatant of transfected cells, isolated by freeze/thaw cycles and centrifugation. The virions may be purified by binding to a heparin-agarose column, eluted, and concentrated. For in vivo delivery, siRNA virions may be purified by fast performance liquid chromatography (FPLC).

The siRNA virions formed from the siRNA vectors may be delivered to target cells of the central or peripheral nervous system, or both, or any target cell from which the therapeutic protein can have an effect on a nervous system disorder or any target cell affected by a synucleinopathy. Preferably, the siRNA virions are added to the cells at the appropriate multiplicity of infection according to standard transduction methods appropriate for the particular target cells. Titers of siRNA virions to administer can vary, depending upon the target cell type and the particular viral vector, and may be determined by those of skill in the art without undue experimentation. siRNA virions are preferably administered to the cell in a therapeutically-effective amount. siRNA virions may be administered in a physiologically acceptable carrier. In general, a "physiologically acceptable carrier" is one that is not toxic or unduly detrimental to cells. Exemplary physiologically acceptable carriers include sterile, pyrogen-free, phosphate buffered saline. Physiologically-acceptable carriers include pharmaceutically-acceptable carriers.

The siRNA virions may be delivered to a target cell by any method known to one of skill in the art, including, but not limited to injection into the delivery site tissue. By way of example, for delivery to a specific region of the central nervous system, the siRNA virions may be administered by microinjection, infusion, convection enhanced delivery (CED), electroporation or other means suitable to directly deliver the composition directly into the delivery site tissue through a surgical incision. The delivery is generally accomplished slowly, such as at a rate of about 0.2-1 .mu.1 per minute. Pursuant to the invention, administration of siRNA virions into selected regions of a subject's brain may be made by drilling a hole and piercing the dura to permit the needle of a microsyringe or micropipette to be inserted. A stereotaxic apparatus may be used to assist in delivering the virions to the specific target cells. Alternatively, siRNA virions may be delivered by lumbar puncture, for example, to the cerebral spinal fluid or delivered intraventricularly. The siRNA virions can be injected intrathecally into a spinal cord region. In another example, virions may be delivered to muscle in order to deliver siRNA to the terminals of motor neurons or sensory neurons. As will be understood by one of skill in the art, virions may be delivered to any cell by any means.

Materials and Methods

Cell Lines and Tissues:

The 28 breast cancer cell lines were cultured as described previously (45). De-identified fresh frozen breast cancer specimens, fresh frozen breast tissue adjacent to tumors, and fresh frozen breast tissue specimens from reduction mammoplasty procedures were obtained from the University of Alabama at Birmingham's Comprehensive Cancer Center Tissue Procurement Shared Facility. The specific aliquots of specimens provided for research were chosen based on their quality control by board certified pathologists. After identification by quality control, the normal uninvolved breast tissue aliquots were not further macro-dissected. The breast tumor specimens were macro-dissected by the pathologists at the Tissue Procurement Shared Facility to enrich for tumor cell content and remove adjacent normal tissue. The frozen breast tissue specimens were weighed, transferred to a 15 mL conical tube containing ceramic beads, and RLT Buffer (Qiagen) plus 1% BME was added so that the tube contained 35 uL of buffer for each milligram of tissue. The conical tubes containing tissue, ceramic beads and buffer were then shaken in a MP Biomedicals FastPrep machine until the tissue was visibly homogenized (90 seconds at 6.5 meters per second). The homogenized tissue was stored at −80° C.

RNA-Seq:

Total RNA was extracted from 5 million cultured cells or 350 uL of tissue homogenate (equivalent to 10 mg of tissue) using the Norgen Animal Tissue RNA Purification Kit (Norgen Biotek Corporation). Cell lysate was treated with Proteinase K before it was applied to the column and on-column DNAse treatment was performed according to the manufacturer's instructions. Total RNA was eluted from the columns and quantified using the Qubit RNA Assay Kit and the Qubit 2.0 fluorometer (Invitrogen). RNA-seq libraries for each sample were constructed from 250 ng total RNA using the polyA selection and transposase-based non-stranded library construction (Tn-RNA-seq) described previously (35). RNA-seq libraries were barcoded during PCR using Nextera barcoded primers according to the manufacturer (Epicentre). The RNA-seq libraries were quantified using the Qubit dsDNA HS Assay Kit and the Qubit 2.0 fluorometer (Invitrogen) and three barcoded libraries were pooled in equimolar quantities for sequencing. The pooled libraries were sequenced on an Illumina HiSeq 2000 sequencing machine using paired-end 50 bp reads and a 6 bp index read, and we obtained at least 50 million read pairs from each library. ChimeraScan 0.4.5a was used to align and identify fusion transcripts in each of the sequencing libraries using default parameters (36). To quantify the expression of each fusion partner, we used TopHat v1.4.1 (46) with the options -r 100—mate-std-dev 75 to align 50 million RNA-seq read pairs, and used GENCODE version 9 (47) as a transcript reference. Gene expression values (Fragments Per Kilobase of transcript Per Million reads, FPKMs) were calculated for each GENCODE transcript using Cufflinks 1.3.0 with the -u option (48).

Splice Junction DNA Sequencing:

Genomic DNA was isolated from 12 breast cancer cell lines using 5 million cultured cells per cell line and the Qiagen DNeasy Kit. PCR amplification of 200 bp surrounding the terminal exon splice acceptor site that is skipped in the formation of the read-through fusion transcripts were performed in 50 uL reactions containing 5 ng genomic DNA, 0.5 uM Forward PCR primer, 0.5 uM Reverse PCR primer, 5 units Platinum Taq DNA Polymerase (Invitrogen), 1×PCR Buffer with 2 mM $MgCl_2$, 0.5 mM each dNTP, and 0.5 M Betaine. These reactions were denatured at 98° C. for 1 minute then thermocycled (30 cycles of 95° C. for 30 seconds and 62° C. for 3 minutes) and held at 4° C. The PCR products were purified using Agencourt AMPure XP beads (Beckman Coulter). The PCR products were quantified using the Qubit dsDNA HS Assay Kit and the Qubit 2.0 fluorometer (Invitrogen). Equimolar quantities of each of the eight PCR products were pooled into 12 pools, one for each cell line. Illumina sequencing libraries were prepared for each of the 12 pools of PCR products using Nextera according to the manufacturer's instructions (Epicentre). The 12 libraries were quantified using the Qubit dsDNA HS Assay Kit and the Qubit 2.0 fluorometer (Invitrogen). Equimolar quantities of each library were pooled and diluted to 10 nM and sequenced using single-end 50 bp reads and a 6 base index read on the Illumina MiSeq sequencer. We obtained 6 million sequencing reads in total covering all 8 amplicons in each of the 12 breast cancer cell lines. Variants were identified by the GATK software on BaseSpace (Illumina) and BAM files were downloaded and inspected manually using IGV 2.0 (49).

Western Blots:

Breast cancer cell pellets containing 2.5 million cells were lysed by adding 100 uL RIPA Buffer (1×PBS, 1% NP-40, 0.5% sodium deoxycholate, 0.1% SDS and Roche protease inhibitor cocktail) and passing the solution through a 21-gauge needle. The lysed cells were then centrifuged at 16,000 rcf for 15 minutes at 4° C., and the supernatant was collected and protein was quantified using the Qubit Protein Assay Kit and the Qubit 2.0 fluorometer (Invitrogen). Twenty micrograms of protein extract was loaded into a BioRad 12% SDS-polyacrylamide gel in 1× Tris/Glycine Buffer (BioRad). Magic Marker (Invitrogen) was used as a protein standard. The gel electrophoresis rig was partially immersed in an ice bath while it ran for 1.5 hours at 125 V. Proteins were transferred to a nitrocellulose membrane using the iBlot system (Invitrogen) for 7 minutes at 20 V. The membranes were washed (lx PBS with 0.05% Tween 20) and incubated in blocking buffer for 60 minutes (lx PBS with 0.05% Tween 20 and 5% w/v Instant Nonfat Dry Milk). The membranes were then incubated with primary antibody overnight at 4° C. (1× PBS with 0.05% Tween 20, 1% w/v Instant Nonfat Dry Milk, and 500 ng/mL primary antibody) followed by three 10 minute washes (1×PBS with 0.05% Tween 20). The following primary antibodies from Santa Cruz Biotechnology were used: CRELD1 sc-99364, CTSD sc-37438, and TNFRSF1A sc-8436. The membrane was then incubated with secondary antibody (1×PBS, 0.05% Tween 20, 1% Instant Nonfat Dry Milk, and a 1:4,000 dilution of horseradish peroxidase (HRP) conjugated goat anti-mouse secondary antibody (Thermo Scientific)). The membrane was then washed (lx PBS with 0.05% Tween 20) and incubated for 5 minutes in a substrate solution of equal parts stable peroxide and luminol/enhancer (SuperSignal West Femto Chemiluminescent Substrate, Thermo Scientific). The membranes were then imaged for chemiluminescence.

qPCR and RNAi

Four ON-TARGETplus custom siRNA duplex reagents from Thermo Scientific were ordered configured to target the fusion junctions of the read-through fusion transcript and ON-TARGETplus Non-targeting siRNA #1 was also purchases (Thermo Scientific catalog ##D-001810-01-05), to serve as a control in experiments. To design the custom siRNAs, entered the fusion junction nucleotide sequences into the siDESIGN Center on the Thermo Scientific website. The software successfully designed a siRNA corresponding to SEQ ID. NOS. 15 and 16 for the CTSD-IFITM10 fusion and a siRNA corresponding to SEQ ID. NOs. 19 and 20 for SCNN1A-TNFRSF1A fusion. The software did not report any other siRNAs to these targets. The fusion junction sequence for CTSD-IFITM10 siRNA #2 and SCNN1A-TNFRSF1A siRNA #2 were then entered and the software design a siRNA corresponding to SEQ ID. NOs. 17 and 18 for the CTSD-IFITM10 fusion and a siRNA corresponding to SEQ ID NOs. 12 and 22 for the SCNN1A-TNFRSF1A fusion, so that we would have a second siRNA targeting each fusion junction sequence with a more even representation of bases on each side of the junction. The siRNA duplex sequences are as follows:

| Sequence | Sense/Anti-Sense | Target Polypeptide | SEQ ID NO |
|---|---|---|---|
| ACUACACGCUCAAGGCCCAUU | Sense | CTSD-IFITM10 | 15 |
| UGGGCCUUGAGCGUGUAGUUU | Anti-sense | CTSD-IFITM10 | 16 |
| ACGCUCAAGGCCCAGGGCCUU | Sense | CTSD-IFITM10 | 17 |
| PGGCCCUGGGCCUUGAGCGUU | Anti-sense | CTSD-IFITM10 | 18 |
| CUGUCACGGUGCUCCUGGAUU | Sense | SCNN1A-TNFRSF1A | 19 |
| PUCCAGGAGCACCGUGACAGUU | Anti-sense | SCNN1A-TNFRSF1A | 20 |
| CUCUGUCACGGUGCUCCUGUU | Sense | SCNN1A-TNFRSF1A | 21 |
| PCAGGAGCACCGUGACAGAGUU | Anti-sense | SCNN1A-TNFRSF1A | 22 |

The MCF7 and HCC1954 cell lines were purchased from ATCC. Both cell lines were cultured in the conditions recommended by ATCC; MCF7 was grown in Eagle's Minimum Essential Medium, supplemented with 0.01 mg/ml bovine insulin and 10% fetal bovine serum; HCC1954 was grown in RPMI-1640 Medium supplemented with 10% fetal bovine serum. The cells were grown in black Costar 96-Well clear-bottom plates (Fisher Scientific catalog #07-200-565). MCF7 was seeded at 15,000 cells per well, and HCC1954 was seeded at 10,000 cells per well.

The siRNA transfection experiments were performed in 96-well plates in triplicate, and included a mock transfection control with no siRNA, a non-targeting siRNA control, and the two custom siRNAs targeting each fusion junction. The Lipofectamine RNAiMAX Transfection Reagent and siRNA were prepared according the manufacturers instruction (Invitrogen). Briefly, 1.5 uL of the transfection reagent was diluted in 25 uL of Opti-MEM I Reduced Serum Medium (Invitrogen) and separately 15 pmol of siRNA stored at 10 uM stock concentration was diluted in 25 uL Opti-MEM I Reduced Serum Medium (Invitrogen). These two dilutions were mixed and incubated at room temperature for 5 minutes. We added 10 uL of the siRNA-transfection reagent mix to each well in the 96-well plate containing cells, which results in 3 pmol of siRNA in 0.3 uL of Lipofectamine RNAiMAX reagent per well.

We ordered PCR primers flanking the fusion junctions of each read-through fusion transcript, as well as primers to the CTCF gene, which were used as a positive control. The primer oligonucleotide sequences are as follows:

| Sequence | Forward/Reverse | Target Polypeptide | SEQ ID NO. |
|---|---|---|---|
| CTACAAGCTGTCCCCAGAGG | Forward | CTSD-IFITM10 | 23 |
| CCGTCCGTGGTGCTG | Reverse | CTSD-IFITM10 | 24 |
| GGCCAAAGTCAACATCTTCTT | Forward | SCNN1A-TNFRSF1A | 25 |
| GGCCAAAGTCAACATCTTCTT | Reverse | SCNN1A-TNFRSF1A | 26 |
| ACCTGTTCCTGTGACTGTACC | Forward | CTCF | 27 |
| ATGGGTTCACTTTCCGCAAGG | Reverse | CTCF | 28 |

We performed the qPCR assay 48 hours after transfection. We prepared cDNA using the Power SYBR Green Cells-to-CT Kit (Invitrogen) according to the manufacturer's instructions, including the option of using 22.5 uL of cell lysate in the reverse transcription reaction. The qPCR experiments were run in duplicate in 10 uL reactions with 4 uL of cDNA, 5 uL Power SYBR Green PCR Master Mix and PCR primers added to a final concentration of 200 nM. For each cDNA sample we also performed control qPCR experiments using 400 nM of each primer designed to CTCF, a housekeeping gene locus that we used to ensure that the quantity and quality of cDNA was equivalent across experiments. The reactions were run on an ABI 7900HT with the following thermal cycling conditions: 50° C. for 2 minutes, 95° C. for 10 minutes, 40 cycles of 95° C. for 15 seconds and 60° C. for 1 min. A dissociation curve analysis was run using the standard protocol on the instrument. Transcript abundance was calculated using automatic baseline and threshold settings using the instrument's software. To calculate the percentage of transcript remaining after siRNA knockdown we normalized the transcript abundance measured in wells treated with siRNAs targeting the fusion junction to the transcript abundance measured in wells treated with the non-targeting siRNA. As a control, we also performed this normalization on the mock transfection with no siRNA to ensure that the presence of the non-targeting siRNA did not affect the abundance of the fusion transcript.

We performed cell proliferation assays 72 hours after transfection using the CyQUANT Cell Proliferation Assay Kit for Cells in Culture (Invitrogen) according to the manufacturers instruction. Our protocol included using 1.5× CyQUANT GR dye, which was recommended to obtain adequate dynamic range in wells with 75,000 cells, which we observed in our untreated controls. The fluorescence from each well of the 96-well plate was measured using the Molecular Devices SpectraMax M5e plate reader. To calculate the percentage of live cells remaining after siRNA knockdown we normalized the fluorescence intensity in wells treated with siRNAs targeting the fusion junction to the fluorescence measured in wells treated with the non-targeting siRNA. As a control, we also performed this normalization on the mock transfection with no siRNA to ensure that the presence of the non-targeting siRNA did not affect the fluorescence or quantity of live of the cells.

REFERENCES

1. Nowell P C. The minute chromosome (Ph1) in chronic granulocytic leukemia. Blut. 1962 April; 8:65-6.
2. Rowley J D. Letter: A new consistent chromosomal abnormality in chronic myelogenous leukaemia identified by quinacrine fluorescence and Giemsa staining. Nature. 1973 Jun. 1; 243(5405):290-3.
3. Rowley J D. Chromosomal translocations: revisited yet again. Blood. 2008 Sep. 15; 112(6):2183-9.
4. Druker B J, Tamura S, Buchdunger E, Ohno S, Segal G M, Fanning S, et al. Effects of a selective inhibitor of the Abl tyrosine kinase on the growth of Bcr-Abl positive cells. Nat Med. 1996 May; 2(5):561-6.
5. Mitelman F, Johansson B, Mertens F. Fusion genes and rearranged genes as a linear function of chromosome aberrations in cancer. Nat Genet. 2004 April; 36(4):331-4.
6. Maher C A, Palanisamy N, Brenner J C, Cao X, Kalyana-Sundaram S, Luo S, et al. Chimeric transcript discovery by paired-end transcriptome sequencing. Proc Natl Acad Sci USA. 2009 Jul. 28; 106(30):12353-8.
7. Tognon C, Knezevich S R, Huntsman D, Roskelley C D, Melnyk N, Mathers J A, et al. Expression of the ETV6-NTRK3 gene fusion as a primary event in human secretory breast carcinoma. Cancer Cell. 2002 November; 2(5):367-76.
8. Persson M, Andren Y, Mark J, Horlings H M, Persson F, Stenman G. Recurrent fusion of MYB and NFIB transcription factor genes in carcinomas of the breast and head and neck. Proc Natl Acad Sci USA. 2009 Nov. 3; 106(44): 18740-4.
9. Tomlins S A, Laxman B, Dhanasekaran S M, Helgeson B E, Cao X, Morris D S, et al. Distinct classes of chromosomal rearrangements create oncogenic ETS gene fusions in prostate cancer. Nature. 2007 Aug. 2; 448(7153):595-9.
10. Tomlins S A, Rhodes D R, Perner S, Dhanasekaran S M, Mehra R, Sun X W, et al. Recurrent fusion of TMPRSS2 and ETS transcription factor genes in prostate cancer. Science. 2005 Oct. 28; 310(5748):644-8.
11. Kumar-Sinha C, Tomlins S A, Chinnaiyan A M. Recurrent gene fusions in prostate cancer. Nat Rev Cancer. 2008 July; 8(7):497-511.
12. Soda M, Choi Y L, Enomoto M, Takada S, Yamashita Y, Ishikawa S, et al. Identification of the transforming EML4-ALK fusion gene in non-small-cell lung cancer. Nature. 2007 Aug. 2; 448(7153):561-6.

13. Robinson D R, Kalyana-Sundaram S, Wu Y M, Shankar S. Cao X, Ateeq B, et al. Functionally recurrent rearrangements of the MAST kinase and Notch gene families in breast cancer. Nat Med. 2011 December; 17(12): 1646-51.

14. Asmann Y W, Hossain A, Necela B M, Middha S, Kalari K R, Sun Z, et al. A novel bioinformatics pipeline for identification and characterization of fusion transcripts in breast cancer and normal cell lines. Nucleic Acids Res. 2011 August; 39(15): e100.

15. Asmann Y W, Necela B M, Kalari K R, Hossain A, Baker T R, Carr J M, et al. Detection of redundant fusion transcripts as biomarkers or disease-specific therapeutic targets in breast cancer. Cancer Res. 2012 Apr. 15; 72(8): 1921-8.

16. Edgren H, Murumagi A, Kangaspeska S, Nicorici D, Hongisto V, Kleivi K, et al. Identification of fusion genes in breast cancer by paired-end RNA-sequencing. Genome Biol. 2011; 12(1): R6.

17. Ha K C, Lalonde E, Li L, Cavallone L, Natrajan R, Lambros M B, et al. Identification of gene fusion transcripts by transcriptome sequencing in BRCA1-mutated breast cancers and cell lines. BMC Med Genomics. 2011; 4:75.

18. Zhao Q, Caballero O L, Levy S, Stevenson B J, Iseli C, de Souza S J, et al. Transcriptome-guided characterization of genomic rearrangements in a breast cancer cell line. Proc Natl Acad Sci USA. 2009 Feb. 10; 106(6):1886-91.

19. Kim D, Salzberg S L. TopHat-Fusion: an algorithm for discovery of novel fusion transcripts. Genome Biol. 2011; 12(8): R72.

20. Frenkel-Morgenstern M, Lacroix V, Ezkurdia I, Levin Y, Gabashvili A, Prilusky J, et al. Chimeras taking shape: potential functions of proteins encoded by chimeric RNA transcripts. Genome Res. 2012 July; 22(7): 1231-42.

21. Li X, Zhao L, Jiang H, Wang W. Short homologous sequences are strongly associated with the generation of chimeric RNAs in eukaryotes. J Mol Evol. 2009 January; 68(1):56-65.

22. Akiva P, Toporik A, Edelheit S, Peretz Y, Diber A, Shemesh R, et al. Transcription-mediated gene fusion in the human genome. Genome Res. 2006 January; 16(1):30-6.

23. Parra G, Reymond A, Dabbouseh N, Dermitzakis E T, Castelo R, Thomson T M, et al. Tandem chimerism as a means to increase protein complexity in the human genome. Genome Res. 2006 January; 16(1):37-44.

24. Li H, Wang J, Ma X, Sklar J. Gene fusions and RNA trans-splicing in normal and neoplastic human cells. Cell Cycle. 2009 Jan. 15; 8(2):218-22.

25. Rickman D S, Pflueger D, Moss B, VanDoren V E, Chen C X, de la Taille A, et al. SLC45A3-ELK4 is a novel and frequent erythroblast transformation-specific fusion transcript in prostate cancer. Cancer Res. 2009 Apr. 1; 69(7):2734-8.

26. Kim R N, Kim A, Choi S H, Kim D S, Nam S H, Kim D W, et al. Novel mechanism of conjoined gene formation in the human genome. Funct Integr Genomics. 2012 March; 12(1):45-61.

27. Prakash T, Sharma V K, Adati N, Ozawa R, Kumar N, Nishida Y, et al. Expression of conjoined genes: another mechanism for gene regulation in eukaryotes. PLoS One. 2010; 5(10): e13284.

28. Kumar-Sinha C, Kalyana-Sundaram S, Chinnaiyan A M. SLC45A3-ELK4 Chimera in Prostate Cancer: Spotlight on cis-Splicing. Cancer Discov. 2012 July; 2(7):582-5.

29. Nacu S, Yuan W, Kan Z, Bhatt D, Rivers C S, Stinson J, et al. Deep RNA sequencing analysis of readthrough gene fusions in human prostate adenocarcinoma and reference samples. BMC Med Genomics. 2011; 4:11.

30. Maher C A, Kumar-Sinha C, Cao X, Kalyana-Sundaram S, Han B, Jing X, et al. Transcriptome sequencing to detect gene fusions in cancer. Nature. 2009 Mar. 5; 458(7234):97-101.

31. Zhang Y, Gong M, Yuan H, Park H G, Frierson H F, Li H. Chimeric Transcript Generated by cis-Splicing of Adjacent Genes Regulates Prostate Cancer Cell Proliferation. Cancer Discov. 2012 July; 2(7):598-607.

32. Kannan K, Wang L, Wang J, Ittmann M M, Li W, Yen L. Recurrent chimeric RNAs enriched in human prostate cancer identified by deep sequencing. Proc Natl Acad Sci USA. 2011 May 31; 108(22):9172-7.

33. Zhou J, Liao J, Zheng X, Shen H. Chimeric RNAs as potential biomarkers for tumor diagnosis. BMB Rep. 2012 March; 45(3):133-40.

34. Stephens P J, McBride D J, Lin M L, Varela I, Pleasance E D, Simpson J T, et al. Complex landscapes of somatic rearrangement in human breast cancer genomes. Nature. 2009 Dec. 24; 462(7276):1005-10.

35. Gertz J, Varley K E, Davis N S, Baas B J, Goryshin I Y, Vaidyanathan R, et al. Transposase mediated construction of RNA-seq libraries. Genome Res. 2012 January; 22(1):134-41.

36. Iyer M K, Chinnaiyan A M, Maher C A. ChimeraScan: a tool for identifying chimeric transcription in sequencing data. Bioinformatics. 2011 Oct. 15; 27(20):2903-4.

37. Wahle E, Ruegsegger U. 3'-End processing of pre-mRNA in eukaryotes. FEMS Microbiol Rev. 1999 June; 23(3):277-95.

38. Martinson H G. An active role for splicing in 3'-end formation. Wiley Interdiscip Rev RNA. 2011 July-August; 2(4):459-70.

39. Kuestner R E, Taft D W, Haran A, Brandt C S, Brender T, Lum K, et al. Identification of the IL-17 receptor related molecule IL-17RC as the receptor for IL-17F. J Immunol. 2007 Oct. 15; 179(8):5462-73.

40. Rupp P A, Fouad G T, Egelston C A, Reifsteck C A, Olson S B, Knosp W M, et al. Identification, genomic organization and mRNA expression of CRELD1, the founding member of a unique family of matricellular proteins. Gene. 2002 Jun. 26; 293(1-2):47-57.

41. Hummler E, Beermann F. Scnn1 sodium channel gene family in genetically engineered mice. J Am Soc Nephrol. 2000 November; 11 Suppl 16:S129-34.

42. Chen G, Goeddel D V. TNF-R1 signaling: a beautiful pathway. Science. 2002 May 31; 296(5573):1634-5.

43. Nicotra G, Castino R, Follo C, Peracchio C, Valente G, Isidoro C. The dilemma: does tissue expression of cathepsin D reflect tumor malignancy? The question: does the assay truly mirror cathepsin D mis-function in the tumor? Cancer Biomark. 2010; 7(1):47-64.

44. Hickford D, Frankenberg S, Shaw G, Renfree M B. Evolution of vertebrate interferon inducible transmembrane proteins. BMC Genomics. 2012; 13:155.

45. Oliver P G, LoBuglio A F, Zhou T, Forero A, Kim H, Zinn K R, et al. Effect of anti-DR5 and chemotherapy on basal-like breast cancer. Breast Cancer Res Treat. 2012 June; 133(2):417-26.

46. Trapnell C, Pachter L, Salzberg S L. TopHat: discovering splice junctions with RNA-Seq. Bioinformatics. 2009 May 1; 25(9):1105-11.

47. Harrow J, Denoeud F, Frankish A, Reymond A, Chen C K, Chrast J, et al. GENCODE: producing a reference annotation for ENCODE. Genome Biol. 2006; 7 Suppl 1:S4 1-9.
48. Trapnell C, Williams B A, Pertea G, Mortazavi A, Kwan G, van Baren M J. et al. Transcript assembly and quantification by RNA-Seq reveals unannotated transcripts and isoform switching during cell differentiation. Nat Biotechnol. 2010 May; 28(5):511-5.
49. Robinson J T, Thorvaldsdottir H, Winckler W, Guttman M, Lander E S, Getz G, et al. Integrative genomics viewer. Nat Biotechnol. 2011 January; 29(1):24-6.

We claim:

1. A method of treating breast cancer in a subject in need thereof, the method comprising:
   (a) detecting the expression of a fusion polypeptide in a sample from the subject, the fusion polypeptide having at least 90% identity with SEQ ID NO: 7;
   (b) diagnosing the subject with a triple-negative breast cancer when the expression of the fusion polypeptide is detected in the sample; and
   (c) administering an effective amount of a breast cancer therapy to the diagnosed subject.

2. The method of claim 1, wherein expression of the fusion polypeptide is detected by detecting the presence of an mRNA encoding the fusion polypeptide in the sample.

3. The method of claim 1, wherein expression of the fusion polypeptide is detected by detecting the presence of an mRNA encoding the fusion polypeptide in the sample by reverse transcription polymerase chain reaction (rtPCR).

4. The method of claim 1, wherein expression of the fusion polypeptide is detected by detecting the presence of the fusion polypeptide in the sample using an immunoassay.

5. The method of claim 1, wherein expression of the fusion polypeptide is detected by detecting the presence of the fusion polypeptide in the sample using an immunoassay selected from one or more of: immunoprecipitation, immunohistochemistry, Western blot analysis, flow cytometry, ELISA, immunoassays with antibody detection, and mass spectrometry.

6. The method of claim 1, wherein the fusion polypeptide has at least 95% identity with SEQ ID NO: 7.

7. The method of claim 1, wherein the fusion polypeptide has at least 99% identity with SEQ ID NO: 7.

8. The method of claim 1, wherein the breast cancer therapy is selected from the group consisting of: a small-molecule drug, an angiogenesis inhibitor, a tumor vaccine, a chemotherapy, an immunotherapy, a monoclonal antibody, radiation therapy, and a gene therapy.

9. A method of treating breast cancer in a subject who has been diagnosed with breast cancer, the method comprising: administering an effective amount of a breast cancer therapy to the diagnosed subject, wherein a fusion polypeptide has been detected in a sample from the subject, the fusion polypeptide having at least 90% identity with SEQ ID NO: 7, and wherein the subject has been diagnosed with a triple-negative breast cancer when the expression of the fusion polypeptide is detected in the sample.

10. The method of claim 9, wherein expression of the fusion polypeptide is detected by detecting the presence of an mRNA encoding the fusion polypeptide in the sample.

11. The method of claim 9, wherein expression of the fusion polypeptide is detected by detecting the presence of an mRNA encoding the fusion polypeptide in the sample by reverse transcription polymerase chain reaction (rtPCR).

12. The method of claim 9, wherein expression of the fusion polypeptide is detected by detecting the presence of the fusion polypeptide in the sample using an immunoassay.

13. The method of claim 9, wherein expression of the fusion polypeptide is detected by detecting the presence of the fusion polypeptide in the sample using an immunoassay selected from one or more of: immunoprecipitation, immunohistochemistry, Western blot analysis, flow cytometry, ELISA, immunoassays with antibody detection, and mass spectrometry.

14. The method of claim 9, wherein the fusion polypeptide has at least 95% identity with SEQ ID NO: 7.

15. The method of claim 9, wherein the fusion polypeptide has at least 99% identity with SEQ ID NO: 7.

16. The method of claim 9, wherein the breast cancer therapy is selected from the group consisting of: a small-molecule drug, an angiogenesis inhibitor, a tumor vaccine, a chemotherapy, an immunotherapy, a monoclonal antibody, radiation therapy, and a gene therapy.

* * * * *

```
                         SEQUENCE LISTING

<160> NUMBER OF SEQ ID NOS: 28

<210> SEQ ID NO 1
<211> LENGTH: 78
<212> TYPE: DNA
<213> ORGANISM: Homo sapiens

<400> SEQUENCE: 1
ctttccctca tcctccttct caaaaaggat cacgcgaaag gtccccagcc tgggtaaaga    60
tggccccatg gcccccga                                                  78

<210> SEQ ID NO 2
<211> LENGTH: 88
<212> TYPE: DNA
<213> ORGANISM: Homo sapiens

<400> SEQUENCE: 2
gagctgaact acaaaaccaa ttctgagtct ccctctgtca cggtgctcct ggagctgttg    60
gtgggaatat acccctcagg ggttattg                                       88

<210> SEQ ID NO 3
<211> LENGTH: 65
<212> TYPE: DNA
<213> ORGANISM: Homo sapiens

<400> SEQUENCE: 3
ctgtccccag aggactacac gctcaaggcc cagggccccg gccagtgccc agccccgctg    60
ggaga                                                                65

<210> SEQ ID NO 4
<211> LENGTH: 18
<212> TYPE: PRT
<213> ORGANISM: Homo sapiens

<400> SEQUENCE: 4

Leu Ser Leu Ile Leu Leu Leu Lys Lys Asp His Ala Lys Gly Pro Gln
1               5                   10                  15

Pro Gly

<210> SEQ ID NO 5
<211> LENGTH: 26
<212> TYPE: PRT
<213> ORGANISM: Homo sapiens

<400> SEQUENCE: 5

Leu Ser Leu Ile Leu Leu Leu Lys Lys Asp His Ala Lys Ser Pro Ala
1               5                   10                  15

Trp Val Lys Met Ala Pro Trp Pro Pro Lys
            20                  25

<210> SEQ ID NO 6
<211> LENGTH: 30
<212> TYPE: PRT
<213> ORGANISM: Homo sapiens
```

```
<400> SEQUENCE: 6

Glu Leu Asn Tyr Lys Thr Asn Ser Glu Ser Pro Ser Val Thr Val Leu
1               5                   10                  15

Leu Glu Leu Leu Val Gly Ile Tyr Pro Ser Gly Val Ile Gly
            20                  25                  30

<210> SEQ ID NO 7
<211> LENGTH: 22
<212> TYPE: PRT
<213> ORGANISM: Homo sapiens

<400> SEQUENCE: 7

Leu Ser Pro Glu Asp Tyr Thr Leu Lys Ala Gln Gly Pro Gly Gln Cys
1               5                   10                  15

Pro Ala Pro Leu Gly Asp
            20

<210> SEQ ID NO 8
<211> LENGTH: 4051
<212> TYPE: DNA
<213> ORGANISM: Homo sapiens

<400> SEQUENCE: 8
acagccagca gcctgccggg agccaaaacg aaagcactcc gtgctggaag taggaggaga      60
gtcaggactc ccaggacaga gagtgcacaa actacccagc acagccccct ccgccccctc     120
tggaggctga gagggattc cagccctgc cacccacaga cacgggctga ctggggtgtc      180
tgccccctt ggggggggc agcacagggc ctcaggcctg gtgccacct ggcacctaga       240
agatgcctgt gcctggttc ttgctgtcct ggcactggg ccgaagccca gtggtccttt      300
ctctggagag gcttgtgggg cctcaggacg ctacccactg ctctccgggc ctctcctgcc    360
gcctctggga cagtgacata ctctgcctgc ctggggacat cgtgcctgct ccgggccccg    420
tgctggcgcc tacgcacctg cagacagagc tggtgctgag gtgccagaag agaccgact     480
gtgacctctg tctgcgtgtg gctgtccact ggccgtgca tgggcactgg gaagagcctg    540
aagatgagga aaagtttgga ggagcagctg actcaggggt ggaggagcct aggaatgcct    600
ctctccaggc ccaagtcgtg ctctccttcc aggcctaccc tactgcccgc tgcgtcctgc    660
tggaggtgca agtgcctgct gcccttgtgc agtttggtca gtctgtgggc tctgtggtat    720
atgactgctt cgaggctgcc ctagggagtg aggtacgaat ctggtcctat actcagccca    780
ggtacgagaa ggaactcaac cacacacagc agctgcctga ctgcagggg ctcgaagtct     840
ggaacagcat cccgagctgc tgggccctgc cctggctcaa cgtgtcagca gatggtgaca    900
acgtgcatct ggttctgaat gtctctgagg agcagcactt cggcctctcc ctgtactgga    960
atcaggtcca gggcccccca aaaccccggt ggcacaaaaa cctgactgga ccgcagatca   1020
ttaccttgaa ccacacagac ctggttccct gcctctgtat tcaggtgtgg cctctggaac   1080
ctgactccgt taggacgaac atctgcccct tcagggagga ccccgcgca caccagaacc   1140
tctggcaagc cgcccgactg cgactgctga ccctgcagag ctggctgctg acgcaccgt    1200
gctcgctgcc cgcagaagcg gcactgtgct ggcgggctcc gggtggggac ccctgccagc   1260
cactggtccc accgctttcc tgggagaacg tcactgtgga caaggttctc gagttcccat   1320
tgctgaaagg ccaccctaac ctctgtgttc aggtgaacag ctcggagaag ctgcagctgc   1380
aggagtgctt gtgggctgac tccctggggc ctctcaaaga cgatgtgcta ctgttggaga   1440
cacgaggccc ccaggacaac agatccctct gtgccttgga acccagtggc tgtacttcac   1500
```

-continued

```
tacccagcaa agcctccacg agggcagctc gccttggaga gtacttacta caagacctgc    1560
agtcaggcca gtgtctgcag ctatgggacg atgacttggg agcgctatgg gcctgcccca    1620
tggacaaata catccacaag cgctgggccc tcgtgtggct ggcctgccta ctctttgccg    1680
ctgcgctttc cctcatcctc cttctcaaaa aggatcacgc gaaaggtccc cagcctgggt    1740
aaagatggcc ccatggcccc cgaagggcct agtcccagct gtgctctggg gcctcagcct    1800
cttcctcaac ctcccaggac ctatctggct ccagccctct ccacctcccc agtcttctcc    1860
cccgcctcag ccccatccgt gtcatacctg ccggggactg gttgacagct ttaacaaggg    1920
cctggagaga accatccggg acaactttgg aggtggaaac actgcctggg aggaagagaa    1980
tttgtccaaa tacaaagaca gtgagacccg cctggtagag gtgctggagg gtgtgtgcag    2040
caagtcagac ttcgagtgcc accgcctgct ggagctgagt gaggagctgg tggagagctg    2100
gtggtttcac aagcagcagg aggccccgga cctcttccag tggctgtgct cagattccct    2160
gaagctctgc tgccccgcag gcaccttcgg gccctcctgc cttccctgtc ctggggggaac   2220
agagaggccc tgcggtggct acgggcagtg tgaaggagaa gggacacgag ggggcagcgg    2280
gcactgtgac tgccaagccg gctacggggg tgaggcctgt ggccagtgtg gccttggcta    2340
ctttgaggca gaacgcaacg ccagccatct ggtatgttcg gcttgttttg gccctgtgc    2400
ccgatgctca ggacctgagg aatcaaactg tttgcaatgc aagaagggct gggccctgca    2460
tcacctcaag tgtgtagaca ttgatgagtg tggcacagag ggagccaact gtggagctga    2520
ccaattctgc gtgaacactg agggctccta tgagtgccga gactgtgcca aggcctgcct    2580
aggctgcatg ggggcagggc caggtcgctg taagaagtgt agccctggct atcagcaggt    2640
gggctccaag tgtctcgatg tggatgagtg tgagacagag gtgtgtccgg gagagaacaa    2700
gcagtgtgaa aacaccgagg gcggttatcg ctgcatctgt ccgagggct acaagcagat    2760
ggaaggcatc tgtgtgaagg agcagatccc aggtgcattc cccatcttaa ctgatttaac    2820
ccctgaaaca acccgacgct ggaagttggg ttctcatccc cactctacat atgtaaaaat    2880
gaagatgcag agagatgaag ctactttccc agggctatat ggcaagcaag tcgcaaagct    2940
gggatcccaa tccagacagt ctgaccgtgg aacgagactc atacacagtc agcaggcttc    3000
ttctcagaga tgacagaaga cgagttggtg gtgctgcagc agatgttctt tggcatcatc    3060
atctgtgcac tggccacgct ggctgctaag ggcgacttgg tgttcaccgc catcttcatt    3120
ggggctgtgg cggccatgac tggctactgg ttgtcagagc gcagtgaccg tgtgctggag    3180
ggcttcatca agggcagata atcgcggcca ccacctgtag gacctcctcc cacccacgct    3240
gcccccagag cttgggctgc cctcctgctg gacactcagg acagcttggt ttattttga    3300
gagtggggta agcaccccta cctgccttac agagcagccc aggtacccag gcccgggcag    3360
acaaggcccc tggggtaaaa agtagccctg aaggtggata ccatgagctc ttcacctggc    3420
ggggactggc aggcttcaca atgtgtgaat ttcaaaagtt tttccttaat ggtggctgct    3480
agagctttgg cccctgctta ggattaggtg gtcctcacag gggtggggcc atcacagctc    3540
cctcctgcca gctgcatgct gccagttcct gttctgtgtt caccacatcc ccacacccca    3600
ttgccactta tttattcatc tcaggaaata aagaaaggtc ttggaaagtt aaaaggcatc    3660
agtcttacta cctgtcccac cacccccacc ttagggaaat gtcctagaat cctgggaaat    3720
tgagggcttc tttgatggtg agtggagaaa agatagagga gaaggttgcc cctgaagtgc    3780
tgttaggaga aggaggatag aggaatcagc cttaggaggg ttccatgcca gctgtcattt    3840
```

```
ggcaaaggac cctggacaga tgactttttgc ctctgaactt cactcttctc tttcctcaaa    3900
tgggcttcat aatgctttcc actcaggctt aacatgagaa ttaaatgagg tgacaaatgt    3960
gaagacctgg acagtacaca acagatattc aataaaagtg tggtcgccat tatgaccaga    4020
gcctccaagc ctcaaaaaaa aaaaaaaaaa a                                    4051
```

<210> SEQ ID NO 9
<211> LENGTH: 922
<212> TYPE: PRT
<213> ORGANISM: Homo sapiens

<400> SEQUENCE: 9

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335
```

```
Pro Cys Gln Pro Leu Val Pro Leu Ser Trp Glu Asn Val Thr Val
            340                 345                 350

Asp Lys Val Leu Glu Phe Pro Leu Leu Lys Gly His Pro Asn Leu Cys
        355                 360                 365

Val Gln Val Asn Ser Ser Glu Lys Leu Gln Leu Gln Glu Cys Leu Trp
    370                 375                 380

Ala Asp Ser Leu Gly Pro Leu Lys Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
            420                 425                 430

Glu Tyr Leu Leu Gln Asp Leu Gln Ser Gly Gln Cys Leu Gln Leu Trp
        435                 440                 445

Asp Asp Asp Leu Gly Ala Leu Trp Ala Cys Pro Met Asp Lys Tyr Ile
    450                 455                 460

His Lys Arg Trp Ala Leu Val Trp Leu Ala Cys Leu Leu Phe Ala Ala
465                 470                 475                 480

Ala Leu Ser Leu Ile Leu Leu Leu Lys Lys Asp His Ala Lys Ser Pro
                485                 490                 495

Ala Trp Val Lys Met Ala Pro Trp Pro Lys Gly Leu Val Pro Ala
            500                 505                 510

Val Leu Trp Gly Leu Ser Leu Phe Leu Asn Leu Pro Gly Pro Ile Trp
        515                 520                 525

Leu Gln Pro Ser Pro Pro Gln Ser Ser Pro Pro Gln Pro His
530                 535                 540

Pro Cys His Thr Cys Arg Gly Leu Val Asp Ser Phe Asn Lys Gly Leu
545                 550                 555                 560

Glu Arg Thr Ile Arg Asp Asn Phe Gly Gly Asn Thr Ala Trp Glu
                565                 570                 575

Glu Glu Asn Leu Ser Lys Tyr Lys Asp Ser Glu Thr Arg Leu Val Glu
        580                 585                 590

Val Leu Glu Gly Val Cys Ser Lys Ser Asp Phe Glu Cys His Arg Leu
    595                 600                 605

Leu Glu Leu Ser Glu Glu Leu Val Glu Ser Trp Trp Phe His Lys Gln
610                 615                 620

Gln Glu Ala Pro Asp Leu Phe Gln Trp Leu Cys Ser Asp Ser Leu Lys
625                 630                 635                 640

Leu Cys Cys Pro Ala Gly Thr Phe Gly Pro Ser Cys Leu Pro Cys Pro
                645                 650                 655

Gly Gly Thr Glu Arg Pro Cys Gly Gly Tyr Gly Gln Cys Glu Gly Glu
        660                 665                 670

Gly Thr Arg Gly Gly Ser Gly His Cys Asp Cys Gln Ala Gly Tyr Gly
    675                 680                 685

Gly Glu Ala Cys Gly Gln Cys Gly Leu Gly Tyr Phe Glu Ala Glu Arg
690                 695                 700

Asn Ala Ser His Leu Val Cys Ser Ala Cys Phe Gly Pro Cys Ala Arg
705                 710                 715                 720

Cys Ser Gly Pro Glu Glu Ser Asn Cys Leu Gln Cys Lys Lys Gly Trp
                725                 730                 735

Ala Leu His His Leu Lys Cys Val Asp Ile Asp Glu Cys Gly Thr Glu
        740                 745                 750

Gly Ala Asn Cys Gly Ala Asp Gln Phe Cys Val Asn Thr Glu Gly Ser
```

|     |     |     |     |     |     |     | 755 |     |     |     | 760 |     |     |     | 765 |     |     |
| --- | --- | --- | --- | --- | --- | --- | --- | --- | --- | --- | --- | --- | --- | --- | --- | --- | --- |

Tyr Glu Cys Arg Asp Cys Ala Lys Ala Cys Leu Gly Cys Met Gly Ala
         770                 775                 780

Gly Pro Gly Arg Cys Lys Lys Cys Ser Pro Gly Tyr Gln Gln Val Gly
785                 790                 795                 800

Ser Lys Cys Leu Asp Val Asp Glu Cys Glu Thr Glu Val Cys Pro Gly
                 805                 810                 815

Glu Asn Lys Gln Cys Glu Asn Thr Glu Gly Gly Tyr Arg Cys Ile Cys
                 820                 825                 830

Ala Glu Gly Tyr Lys Gln Met Glu Gly Ile Cys Val Lys Glu Gln Ile
                 835                 840                 845

Pro Gly Ala Phe Pro Ile Leu Thr Asp Leu Thr Pro Glu Thr Thr Arg
        850                 855                 860

Arg Trp Lys Leu Gly Ser His Pro His Ser Thr Tyr Val Lys Met Lys
865                 870                 875                 880

Met Gln Arg Asp Glu Ala Thr Phe Pro Gly Leu Tyr Gly Lys Gln Val
                 885                 890                 895

Ala Lys Leu Gly Ser Gln Ser Arg Gln Ser Asp Arg Gly Thr Arg Leu
         900                 905                 910

Ile His Ser Gln Gln Ala Ser Ser Gln Arg
         915                 920

```
<210> SEQ ID NO 10
<211> LENGTH: 3834
<212> TYPE: DNA
<213> ORGANISM: Homo sapiens

<400> SEQUENCE: 10
cttgcctgtc tgcgtctaaa gccctgccc  agagtccgcc ttctcaggtc cagtactccc    60
agttcacctg ccctcgggag ccctccttcc ttcggaaaac tcccggctct gactcctcct   120
cagcccctcc ccccgccctg ctcacccttta attgagatgc taatgagatt cctgtcgctt   180
ccatccctgg ccggccagcg ggcgggctcc ccagccaggc cgctgcacct gtcaggggaa   240
caagctggag gagcaggacc ctagacctct gcagcccata ccaggtctca tggaggggaa   300
caagctggag gagcaggact ctagccctcc acagtccact ccagggctca tgaaggggaa   360
caagcgtgag gagcagggc tgggccccga acctgcggcg ccccagcagc ccacggcgga   420
ggaggaggcc ctgatcgagt ccaccgctc ctaccgagag ctcttcgagt tcttctgcaa   480
caacaccacc atccacggcg ccatccgcct ggtgtgctcc cagcacaacc gcatgaagac   540
ggccttctgg gcagtgctgt ggctctgcac ctttggcatg atgtactggc aattcggcct   600
gcttttcgga gagtacttca gctaccccgt cagcctcaac atcaacctca actcggacaa   660
gctcgtcttc cccgcagtga ccatctgcac cctcaatccc tacaggtacc cggaaattaa   720
agaggagctg gaggagctgg accgcatcac agagcagacg ctctttgacc tgtacaaata   780
cagctccttc accactctcg tggccggctc ccgcagccgt cgcgacctgc ggggactct   840 gccgcacccc ttgcagcgcc tgagggtccc gccccgcct cacggggccc gtcgagcccg   900
tagcgtggcc tccagcttgc gggacaacaa ccccaggtg gactgaagg actgaagat   960 cggcttccag ctgtgcaacc agaacaaatc ggactgcttc taccagacat actcatcagg  1020
ggtggatgcg gtgagggagt ggtaccgctt ccactacatc aacatcctgt cgaggctgcc  1080
agagactctg ccatccctgg aggaggacac gctgggcaac ttcatcttcg cctgccgctt  1140
caaccaggtc tcctgcaacc aggcgaatta ctctcacttc caccacccga tgtatggaaa  1200
```

```
ctgctatact ttcaatgaca agaacaactc caacctctgg atgtcttcca tgcctggaat   1260
caacaacggt ctgtccctga tgctgcgcgc agagcagaat gacttcattc cctgctgtc    1320 cacagtgact ggggcccggg taatggtgca cgggcaggat gaacctgcct ttatggatga   1380
tggtggcttt aacttgcggc ctggcgtgga gacctccatc agcatgagga aggaaaccct   1440
ggacagactt gggggcgatt atggcgactg caccaagaat ggcagtgatg ttcctgttga   1500
gaacctttac ccttcaaagt acacacagca ggtgtgtatt cactcctgct tccaggagag   1560
catgatcaag gagtgtggct gtgcctacat cttctatccg cggccccaga acgtggagta   1620
ctgtgactac agaaagcaca gttcctgggg gtactgctac tataagctcc aggttgactt   1680
ctcctcagac cacctgggct gtttcaccaa gtgccggaag ccatgcagcg tgaccagcta   1740
ccagctctct gctggttact cacgatggcc ctcggtgaca tcccaggaat gggtcttcca   1800
gatgctatcg cgacagaaca attacaccgt caacaacaag agaaatggag tggccaaagt   1860
caacatcttc ttcaaggagc tgaactacaa aaccaattct gagtctccct ctgtcacggt   1920
gctcctggag ctgttggtgg aatatacccc tcagggggtt attggactgg tccctcacct   1980
aggggacagg gagaagagag atagtgtgtg tccccaagga aaatatatcc accctcaaaa   2040
taattcgatt tgctgtacca agtgccacaa aggaacctac ttgtacaatg actgtccagg   2100
cccggggcag gatacggact gcaggggagtg tgagagcggc tccttcaccg cttcagaaaa   2160
ccacctcaga cactgcctca gctgctccaa atgccgaaag gaaatgggtc aggtggagat   2220
ctcttcttgc acagtggacc gggacaccgt gtgtggctgc aggaagaacc agtaccggca   2280
ttattggagt gaaaaccttt tccagtgctt caattgcagc ctctgcctca atgggaccgt   2340
gcacctctcc tgccaggaga acagaacac cgtgtgcacc tgccatgcag gtttctttct     2400
aagagaaaac gagtgtgtct cctgtagtaa ctgtaagaaa agcctggagt gcacgaagtt   2460
gtgcctaccc cagattgaga atgttaaggg cactgaggac tcaggcacca cagtgctgtt   2520 gccctggtc atttttctttg gtctttgcct tttatccctc ctcttcattg gtttaatgta    2580
tcgctaccaa cggtggaagt ccaagctcta ctccattgtt tgtgggaaat cgacacctga   2640
aaaagagggg gagcttgaag gaactactac taagcccctg gccccaaacc caagcttcag   2700
tcccactcca ggcttcaccc ccaccctggg cttcagtccc gtgcccagtt ccaccttcac   2760
ctccagctcc acctataccc ccggtgactg tcccaacttt gcggctcccc gcagagaggt   2820
ggcaccaccc tatcaggggg ctgaccccat ccttgcgaca gccctcgcct ccgaccccat   2880
ccccaacccc cttcagaagt gggaggacag cgcccacaag ccacagagcc tagacactga   2940
tgaccccgcg acgctgtacg ccgtggtgga gaacgtgccc ccgttgcgct ggaaggaatt   3000
cgtgcggcgc ctaggctga cgaccacga gatcgatcgg ctggagctgc agaacgggcg    3060
ctgcctgcgc gaggcgcaat acagcatgct ggcgacctgg aggcggcgca cgccgcggcg   3120
cgaggccacg ctggagctgc tgggacgcgt gctccgcgac atggacctgc tgggctgcct   3180
ggaggacatc gaggaggcgc tttgcggccc cgccgccctc cgcccgcgc ccagtcttct    3240 cagatgagc tgcgccctg cgggcagctc taaggaccgt cctgcgagat cgccttccaa     3300
ccccactttt ttctgaaaag gagggtcct gcaggggcaa gcaggagcta gcagccgcct    3360
acttggtgct aaccctcga tgtacatagc ttttctcagc tgcctgcgcg ccgccgacag   3420
tcagcgctgt gcgcgcggag agaggtcgcg cgtgggctca agagcctgag tgggtggttt   3480
gcgaggatga gggacgctat gcctcatgcc cgttttgggt gtcctcacca gcaaggctgc   3540
```

-continued

```
tcggggccc ctggttcgtc cctgagcctt tttcacagtg cataagcagt ttttttttgtt    3600 tttgttttgt tttgttttgt ttttaaatca atcatgttac actaatagaa acttggcact    3660
cctgtgccct ctgcctggac aagcacatag caagctgaac tgtcctaagg cagggggcgag   3720 cacggaacaa tggggccttc agctggagct gtggactttt gtacatacac taaaattctg    3780
aagttaaagc tctgctcttg gaaaaaaaaa aaaaaaaaaa aaaaaaaaaa aaaa          3834
```

<210> SEQ ID NO 11
<211> LENGTH: 985
<212> TYPE: PRT
<213> ORGANISM: Homo sapiens

<400> SEQUENCE: 11

| Met | Glu | Gly | Asn | Lys | Leu | Glu | Glu | Gln | Asp | Ser | Pro | Pro | Gln | Ser |
|---|---|---|---|---|---|---|---|---|---|---|---|---|---|---|
| 1 | | | | 5 | | | | | 10 | | | | | 15 |

| Thr | Pro | Gly | Leu | Met | Lys | Gly | Asn | Lys | Arg | Glu | Glu | Gln | Gly | Leu | Gly |
|---|---|---|---|---|---|---|---|---|---|---|---|---|---|---|---|
| | | | | 20 | | | | 25 | | | | | 30 | | |

| Pro | Glu | Pro | Ala | Ala | Pro | Gln | Gln | Pro | Thr | Ala | Glu | Glu | Ala | Leu |
|---|---|---|---|---|---|---|---|---|---|---|---|---|---|---|
| | | 35 | | | | 40 | | | | | 45 | | | |

| Ile | Glu | Phe | His | Arg | Ser | Tyr | Arg | Glu | Leu | Phe | Glu | Phe | Phe | Cys | Asn |
|---|---|---|---|---|---|---|---|---|---|---|---|---|---|---|---|
| | 50 | | | | | 55 | | | | | 60 | | | | |

| Asn | Thr | Thr | Ile | His | Gly | Ala | Ile | Arg | Leu | Val | Cys | Ser | Gln | His | Asn |
|---|---|---|---|---|---|---|---|---|---|---|---|---|---|---|---|
| 65 | | | | | 70 | | | | 75 | | | | | 80 | |

| Arg | Met | Lys | Thr | Ala | Phe | Trp | Ala | Val | Leu | Trp | Leu | Cys | Thr | Phe | Gly |
|---|---|---|---|---|---|---|---|---|---|---|---|---|---|---|---|
| | | | | 85 | | | | 90 | | | | | 95 | | |

| Met | Met | Tyr | Trp | Gln | Phe | Gly | Leu | Leu | Phe | Gly | Glu | Tyr | Phe | Ser | Tyr |
|---|---|---|---|---|---|---|---|---|---|---|---|---|---|---|---|
| | | | 100 | | | | | 105 | | | | | 110 | | |

| Pro | Val | Ser | Leu | Asn | Ile | Asn | Leu | Asn | Ser | Asp | Lys | Leu | Val | Phe | Pro |
|---|---|---|---|---|---|---|---|---|---|---|---|---|---|---|---|
| | | 115 | | | | | 120 | | | | | 125 | | | |

| Ala | Val | Thr | Ile | Cys | Thr | Leu | Asn | Pro | Tyr | Arg | Tyr | Pro | Glu | Ile | Lys |
|---|---|---|---|---|---|---|---|---|---|---|---|---|---|---|---|
| | 130 | | | | | 135 | | | | | 140 | | | | |

| Glu | Glu | Leu | Glu | Glu | Leu | Asp | Arg | Ile | Thr | Glu | Gln | Thr | Leu | Phe | Asp |
|---|---|---|---|---|---|---|---|---|---|---|---|---|---|---|---|
| 145 | | | | | 150 | | | | 155 | | | | | 160 | |

| Leu | Tyr | Lys | Tyr | Ser | Ser | Phe | Thr | Thr | Leu | Val | Ala | Gly | Ser | Arg | Ser |
|---|---|---|---|---|---|---|---|---|---|---|---|---|---|---|---|
| | | | | 165 | | | | | 170 | | | | | 175 | |

| Arg | Arg | Asp | Leu | Arg | Gly | Thr | Leu | Pro | His | Pro | Leu | Gln | Arg | Leu | Arg |
|---|---|---|---|---|---|---|---|---|---|---|---|---|---|---|---|
| | | | 180 | | | | | 185 | | | | | 190 | | |

| Val | Pro | Pro | Pro | Pro | His | Gly | Ala | Arg | Arg | Ala | Arg | Ser | Val | Ala | Ser |
|---|---|---|---|---|---|---|---|---|---|---|---|---|---|---|---|
| | | 195 | | | | | 200 | | | | | 205 | | | |

| Ser | Leu | Arg | Asp | Asn | Asn | Pro | Gln | Val | Asp | Trp | Lys | Asp | Trp | Lys | Ile |
|---|---|---|---|---|---|---|---|---|---|---|---|---|---|---|---|
| | 210 | | | | | 215 | | | | | 220 | | | | |

| Gly | Phe | Gln | Leu | Cys | Asn | Gln | Asn | Lys | Ser | Asp | Cys | Phe | Tyr | Gln | Thr |
|---|---|---|---|---|---|---|---|---|---|---|---|---|---|---|---|
| 225 | | | | | 230 | | | | 235 | | | | | 240 | |

| Tyr | Ser | Ser | Gly | Val | Asp | Ala | Val | Arg | Glu | Trp | Tyr | Arg | Phe | His | Tyr |
|---|---|---|---|---|---|---|---|---|---|---|---|---|---|---|---|
| | | | | 245 | | | | | 250 | | | | | 255 | |

| Ile | Asn | Ile | Leu | Ser | Arg | Leu | Pro | Glu | Thr | Leu | Pro | Ser | Leu | Glu | Glu |
|---|---|---|---|---|---|---|---|---|---|---|---|---|---|---|---|
| | | | 260 | | | | | 265 | | | | | 270 | | |

| Asp | Thr | Leu | Gly | Asn | Phe | Ile | Phe | Ala | Cys | Arg | Phe | Asn | Gln | Val | Ser |
|---|---|---|---|---|---|---|---|---|---|---|---|---|---|---|---|
| | | 275 | | | | | 280 | | | | | 285 | | | |

| Cys | Asn | Gln | Ala | Asn | Tyr | Ser | His | Phe | His | His | Pro | Met | Tyr | Gly | Asn |
|---|---|---|---|---|---|---|---|---|---|---|---|---|---|---|---|
| | 290 | | | | | 295 | | | | | 300 | | | | |

| Cys | Tyr | Thr | Phe | Asn | Asp | Lys | Asn | Asn | Ser | Asn | Leu | Trp | Met | Ser | Ser |
|---|---|---|---|---|---|---|---|---|---|---|---|---|---|---|---|
| 305 | | | | | 310 | | | | 315 | | | | | 320 | |

| Met | Pro | Gly | Ile | Asn | Asn | Gly | Leu | Ser | Leu | Met | Leu | Arg | Ala | Glu | Gln |
|---|---|---|---|---|---|---|---|---|---|---|---|---|---|---|---|

```
                325                 330                 335
Asn Asp Phe Ile Pro Leu Leu Ser Thr Val Thr Gly Ala Arg Val Met
            340                 345                 350
Val His Gly Gln Asp Glu Pro Ala Phe Met Asp Asp Gly Gly Phe Asn
            355                 360                 365
Leu Arg Pro Gly Val Glu Thr Ser Ile Ser Met Arg Lys Glu Thr Leu
            370                 375                 380
Asp Arg Leu Gly Gly Asp Tyr Gly Asp Cys Thr Lys Asn Gly Ser Asp
385                 390                 395                 400
Val Pro Val Glu Asn Leu Tyr Pro Ser Lys Tyr Thr Gln Gln Val Cys
                405                 410                 415
Ile His Ser Cys Phe Gln Glu Ser Met Ile Lys Glu Cys Gly Cys Ala
                420                 425                 430
Tyr Ile Phe Tyr Pro Arg Pro Gln Asn Val Glu Tyr Cys Asp Tyr Arg
                435                 440                 445
Lys His Ser Ser Trp Gly Tyr Cys Tyr Tyr Lys Leu Gln Val Asp Phe
            450                 455                 460
Ser Ser Asp His Leu Gly Cys Phe Thr Lys Cys Arg Lys Pro Cys Ser
465                 470                 475                 480
Val Thr Ser Tyr Gln Leu Ser Ala Gly Tyr Ser Arg Trp Pro Ser Val
                485                 490                 495
Thr Ser Gln Glu Trp Val Phe Gln Met Leu Ser Arg Gln Asn Asn Tyr
            500                 505                 510
Thr Val Asn Asn Lys Arg Asn Gly Val Ala Lys Val Asn Ile Phe Phe
            515                 520                 525
Lys Glu Leu Asn Tyr Lys Thr Asn Ser Glu Ser Pro Ser Val Thr Val
            530                 535                 540
Leu Leu Glu Leu Leu Val Gly Ile Tyr Pro Ser Gly Val Ile Gly Leu
545                 550                 555                 560
Val Pro His Leu Gly Asp Arg Glu Lys Arg Asp Ser Val Cys Pro Gln
                565                 570                 575
Gly Lys Tyr Ile His Pro Gln Asn Asn Ser Ile Cys Cys Thr Lys Cys
            580                 585                 590
His Lys Gly Thr Tyr Leu Tyr Asn Asp Cys Pro Gly Pro Gly Gln Asp
            595                 600                 605
Thr Asp Cys Arg Glu Cys Glu Ser Gly Ser Phe Thr Ala Ser Glu Asn
            610                 615                 620
His Leu Arg His Cys Leu Ser Cys Ser Lys Cys Arg Lys Glu Met Gly
625                 630                 635                 640
Gln Val Glu Ile Ser Ser Cys Thr Val Asp Arg Asp Thr Val Cys Gly
                645                 650                 655
Cys Arg Lys Asn Gln Tyr Arg His Tyr Trp Ser Glu Asn Leu Phe Gln
                660                 665                 670
Cys Phe Asn Cys Ser Leu Cys Leu Asn Gly Thr Val His Leu Ser Cys
                675                 680                 685
Gln Glu Lys Gln Asn Thr Val Cys Thr Cys His Ala Gly Phe Phe Leu
            690                 695                 700
Arg Glu Asn Glu Cys Val Ser Cys Ser Asn Cys Lys Lys Ser Leu Glu
705                 710                 715                 720
Cys Thr Lys Leu Cys Leu Pro Gln Ile Glu Asn Val Lys Gly Thr Glu
                725                 730                 735
Asp Ser Gly Thr Thr Val Leu Leu Pro Leu Val Ile Phe Phe Gly Leu
            740                 745                 750
```

Cys Leu Leu Ser Leu Leu Phe Ile Gly Leu Met Tyr Arg Tyr Gln Arg
            755                 760                 765

Trp Lys Ser Lys Leu Tyr Ser Ile Val Cys Gly Lys Ser Thr Pro Glu
770                 775                 780

Lys Glu Gly Glu Leu Glu Gly Thr Thr Thr Lys Pro Leu Ala Pro Asn
785                 790                 795                 800

Pro Ser Phe Ser Pro Thr Pro Gly Phe Thr Pro Thr Leu Gly Phe Ser
                805                 810                 815

Pro Val Pro Ser Ser Thr Phe Thr Ser Ser Ser Thr Tyr Thr Pro Gly
                820                 825                 830

Asp Cys Pro Asn Phe Ala Ala Pro Arg Arg Glu Val Ala Pro Pro Tyr
                835                 840                 845

Gln Gly Ala Asp Pro Ile Leu Ala Thr Ala Leu Ala Ser Asp Pro Ile
850                 855                 860

Pro Asn Pro Leu Gln Lys Trp Glu Asp Ser Ala His Lys Pro Gln Ser
865                 870                 875                 880

Leu Asp Thr Asp Asp Pro Ala Thr Leu Tyr Ala Val Val Glu Asn Val
                885                 890                 895

Pro Pro Leu Arg Trp Lys Glu Phe Val Arg Arg Leu Gly Leu Ser Asp
            900                 905                 910

His Glu Ile Asp Arg Leu Glu Leu Gln Asn Gly Arg Cys Leu Arg Glu
            915                 920                 925

Ala Gln Tyr Ser Met Leu Ala Thr Trp Arg Arg Arg Thr Pro Arg Arg
930                 935                 940

Glu Ala Thr Leu Glu Leu Leu Gly Arg Val Leu Arg Asp Met Asp Leu
945                 950                 955                 960

Leu Gly Cys Leu Glu Asp Ile Glu Glu Ala Leu Cys Gly Pro Ala Ala
                965                 970                 975

Leu Pro Pro Ala Pro Ser Leu Leu Arg
            980                 985

<210> SEQ ID NO 12
<211> LENGTH: 4689
<212> TYPE: DNA
<213> ORGANISM: Homo sapiens

<400> SEQUENCE: 12
gcgcacgccg ccgcgcccca cgtgaccggt ccgggtgcaa acacgcgggt cagctgatcc    60
ggcccaactg cggcgtcatc ccggctataa gcgcacggcc tcggcgaccc tctccgaccc   120
ggccgccgcc gccatgcagc cctccagcct tctgccgctc gccctctgcc tgctggctgc   180
acccgcctcc gcgctcgtca ggatcccgct gcacaagttc acgtccatcc gccggaccat   240
gtcggaggtt gggggctctg tgaggaccct gattgccaaa ggccccgtct caaagtactc   300
ccaggcggtg ccagccgtga ccgaggggcc cattcccgag gtgctcaaga actacatgga   360
cgcccagtac tacgggggaga ttggcatcgg gacgcccccc cagtgcttca gtcgtcgtctt   420 cgacacgggc tcctccaacc tgtgggtccc ctccatccac tgcaaactgc tggacatcgc   480
ttgctggatc caccacaagt acaacagcga caagtccagc acctacgtga agaatggtac   540
ctcgtttgac atccactatg gctcgggcag cctctccggg tacctgagcc aggacactgt   600
gtcggtgccc tgccagtcag cgtcgtcagc ctctgccctg gcggtgtcaa agtggagag    660 gcaggtcttt ggggaggcca ccaagcagcc aggcatcacc ttcatcgcag ccaagttcga   720
tggcatcctg ggcatggcct accccgcat ctccgtcaac aacgtgctgc ccgtcttcga   780

-continued

```
caacctgatg cagcagaagc tggtggacca gaacatcttc tccttctacc tgagcaggga    840
cccagatgcg cagcctgggg gtgagctgat gctgggtggc acagactcca agtattacaa    900
gggttctctg tcctacctga atgtcacccg caaggcctac tggcaggtcc acctggacca    960
ggtggaggtg gccagcgggc tgaccctgtg caaggagggc tgtgaggcca ttgtggacac    1020
aggcacttcc ctcatggtgg gcccggtgga tgaggtgcgc gagctgcaga aggccatcgg    1080
ggccgtgccg ctgattcagg gcgagtacat gatcccctgt gagaaggtgt ccaccctgcc    1140
cgcgatcaca ctgaagctgg gaggcaaagg ctacaagctg tccccagagg actacacgct    1200
caaggcccag ggccccggcc agtgcccagc ccgctgggga gacccggcca gcaccacgga    1260
cggcgcccag gaagcccgag tcccctggac cggggccttc tggattccga ggccccggc     1320
aggttcgccc aagggctgct tcgcttgcgt gtccaagccc cctgccctgc aggctccggc    1380
ggcccctgcc cctgagccct cggcctctcc cccgatggcg cccacactgt tccccatgga    1440
gtccaagagc agcaagaccg acagcgtgcg ggctgccggc gcgcccctg cctgcaagca     1500
cctagccgag aagaagacga tgaccaaccc cacgaccgtc atcgaggtct acccggacac    1560
caccgaggtg aacgactatt acctgtggtc catcttcaac ttcgtctacc tcaacttctg    1620
ctgcctgggc ttcatcgcct tggcctactc cctcaaagtg cgagacaaga agcttctcaa    1680
tgacctgaat ggagccgtgg aggatgcaaa cggacccgg ctgttcaaca tcaccagttc     1740
tgccctggca gcctcctgca tcatcctcgt ctttcatcttc ctgcggtacc ccctcaccga   1800
ctactaaggc ccgccaggca cggctgctgg cggagacaag cactgagaca tgtttattct    1860
catggtccct gaaacgcagg atcccatgag gttggggcag ggcagggctt cttgtcctgg    1920
ggccccttg agctgtgaac tgggcagcaa ggccatcaga agctgagtac agcaagggg      1980
cagtgagctt ggccctcagt ccaccccctc cgcctcctgg cctccaccct gcctgtgtct    2040
ggggcctggg ggcttctccc ctcgctgctg caccctggct tccagcgtct gtgtccctgc    2100
cctcacgtgc cccttcccag gctcctgggg ccccttggac ctgacaccta gcaggaaggg    2160
cttatgcaaa attgtcccag gttgggagga ctcactctgt gctccccgac cctgcctcct    2220
ccacgatgtg accccgctca gagcccttgt gtctgtgaac tttcaatgaa atacccatgc    2280
agctccagcc cagccttcta cttttgtgtcc ctggcagggc ctggagaagt ctggaggctt   2340
tgcaatcctc cctcaggaac tgcctggcgg tcagggcccc gggtgctgtg tcccaacaga    2400
ctgcagggga cggtctgctc catcacagct gtgccagaca gtgaatggga aggggggca     2460
tttggtggag gtaccccaaa ctcgagtcac ttagagggtc aggcagcctc ctgggggac     2520
ggaagggggt ggggcacagc ctcagctgcc tgcattggcc aaatcagagc aaaggaaacc    2580
acaaattcac tcggaaggaa gcagcaggca gagacgatag acgcctggct aaccctgtc     2640
cctcctggag ggctctggga cctggacagg ccccttttacc tctctcgtgc ccatctcctt   2700
agctgtaaaa taggaaaatg gcctttcact tctataatca ctgtgaaaat gaacggaaga    2760
tgcctttcaa aggccgaggc cagcgccctg acggcccatg gcatgtgcag tccacaatgt    2820
gggaggcagg atgcagggat gggctctgtc cccttggaac tcaggcacag tcatgggggt    2880
gccggtcagc cctgaagaca agctgatgag ggtgcactag gaaaagtgca gggcatcggc    2940
gaggcacacg aaggaggtgg ggaggtgaag atggagaaga agccgaggca gtggccatgg    3000
gtgtggagct tcgcgctgtg ggtgcccagc tggtctggga aaccgcagga aatcccgcag    3060
ctcaggtgcg cagtgggaag gacttgctat tccgtgggaa ggcaggcaaa ccttcccagg    3120
```

```
gaaggggcat ggccgtgcgc ctcatgtttt gggaagctcg tgccctctgg ggtagcgagg    3180
ccagcttgga ggggagtcca gtggacagag gtggatgcaa gtggagggag ctgagcctgg    3240
gctggggctg gcagcagagg gctggacagc agggcgcctg cgtggcagct gtgcagtcag    3300
tggggttgac tggtttggaa ggtaaggtgg gggagaagcc cggaggattc ctgtcccttg    3360
acttggacag cccagtggag agggctgtgt accaagggca ggaaaccagg gagaagaaga    3420
tgttgacttt aagataccaa gcagagaagg gaagagcctt ctgggctgga gacgtggggt    3480
gcctcagaag ggaggacctt gagctagcag cagatgggac aaacgcaggg gacagggcac    3540
agccgtggca ggagtgcagc gagcaagatt ctggtcacag tcctgaccca gaaacctgca    3600
gaggaaggga gggtggccag cacctgcccg tgggcctggg gtgcagccca ggcagaggtg    3660
gatgcagggg gtgctcaggg aagaggggag gggagtgtgt gacctcaaaa tgggagggct    3720
tgggggtcag agtcgagaga ggggacaggg tgggaccat gtgggactct tgagcactga     3780
cccttgaacc caggcagtgg tgggatggga gggcaggagg cggcgggctg cgaggctgat    3840
gcggggctgc acggagctgt cattgagcct cttggaggat ggtgggagaa gtgccagggg    3900
cggctgaaag ccttgccgag actgtgggca gcctggttgt gggcacttcg gatgcttgca    3960
ccattagacc cagaggcttc ctggacaagc ctgggctgga agaggatggc agaggctgct    4020
gggccttgga agagagggg tcctggcttc tagttcctgg ggcagctaag gccaacccca    4080
gtgtccaggt gtcttccatg ttatgcctgg gagggaagaa agtagagggg caaatgcttt    4140
ctttgcctat tttccttaaa catttggtgg cagtgctggt ggctgcctgg acaggggcc    4200
aggaggaaac acccctgcat tagggaagcc ctcagccagc ttttccctgg gatgttcctg    4260
cgcctggctg aagctttctg agttcatgtt ggggaaatgg aacggtcacc ttccagccag    4320
taaaggcacc cctagctctt gggatgtttg tatccaactc cgggcaatgt ggggctacaa    4380
aggcccctgg cttccatacc ctggggaccg ggggagggct ggtgctcccg cggtgggtgt    4440
ccacggtgag gtcaggcccc cacagcaggt gcattctcgc cctcagcagg caggcaagca    4500
ggcatcagct ccggcgctgg tctctggctt cgaagtctgt gtctttgcct gtctgtactc    4560
atgcctgacc tgctggcgct ccctgtccac tgcactcctc ccacctcatt tttatgtgat    4620
tttgcacagt gcctggcaga catttgacat tcaataaaca ttgtacgaac gaaagaaaaa    4680
aaaaaaaa                                                            4689
```

<210> SEQ ID NO 13
<211> LENGTH: 557
<212> TYPE: PRT
<213> ORGANISM: Homo sapiens

<400> SEQUENCE: 13

```
Met Gln Pro Ser Ser Leu Leu Pro Leu Ala Leu Cys Leu Leu Ala Ala
1               5                   10                  15

Pro Ala Ser Ala Leu Val Arg Ile Pro Leu His Lys Phe Thr Ser Ile
            20                  25                  30

Arg Arg Thr Met Ser Glu Val Gly Gly Ser Val Glu Asp Leu Ile Ala
        35                  40                  45

Lys Gly Pro Val Ser Lys Tyr Ser Gln Ala Val Pro Ala Val Thr Glu
    50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
                85                  90                  95
```

```
Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
        115                 120                 125

Ser Thr Tyr Val Lys Asn Gly Thr Ser Phe Asp Ile His Tyr Gly Ser
    130                 135                 140

Gly Ser Leu Ser Gly Tyr Leu Ser Gln Asp Thr Val Ser Val Pro Cys
145                 150                 155                 160

Gln Ser Ala Ser Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
        195                 200                 205

Asn Asn Val Leu Pro Val Phe Asp Asn Leu Met Gln Gln Lys Leu Val
    210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
            260                 265                 270

His Leu Asp Gln Val Glu Val Ala Ser Gly Leu Thr Leu Cys Lys Glu
        275                 280                 285

Gly Cys Glu Ala Ile Val Asp Thr Gly Thr Ser Leu Met Val Gly Pro
    290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335

Ala Ile Thr Leu Lys Leu Gly Gly Lys Gly Tyr Lys Leu Ser Pro Glu
            340                 345                 350

Asp Tyr Thr Leu Lys Ala Gln Gly Pro Gly Gln Cys Pro Ala Pro Leu
        355                 360                 365

Gly Asp Pro Ala Ser Thr Thr Asp Gly Ala Gln Glu Ala Arg Val Pro
    370                 375                 380

Leu Asp Gly Ala Phe Trp Ile Pro Arg Pro Ala Gly Ser Pro Lys
385                 390                 395                 400

Gly Cys Phe Ala Cys Val Ser Lys Pro Pro Ala Leu Gln Ala Pro Ala
                405                 410                 415

Ala Pro Ala Pro Glu Pro Ser Ala Ser Pro Met Ala Pro Thr Leu
            420                 425                 430

Phe Pro Met Glu Ser Lys Ser Ser Lys Thr Asp Ser Val Arg Ala Ala
        435                 440                 445

Gly Ala Pro Pro Ala Cys Lys His Leu Ala Glu Lys Lys Thr Met Thr
    450                 455                 460

Asn Pro Thr Thr Val Ile Glu Val Tyr Pro Asp Thr Thr Glu Val Asn
465                 470                 475                 480

Asp Tyr Tyr Leu Trp Ser Ile Phe Asn Phe Val Tyr Leu Asn Phe Cys
                485                 490                 495

Cys Leu Gly Phe Ile Ala Leu Ala Tyr Ser Leu Lys Val Arg Asp Lys
            500                 505                 510
```

Lys Leu Leu Asn Asp Leu Asn Gly Ala Val Glu Asp Ala Lys Thr Ala
            515                 520                 525

Arg Leu Phe Asn Ile Thr Ser Ser Ala Leu Ala Ala Ser Cys Ile Ile
530                 535                 540

Leu Val Phe Ile Phe Leu Arg Tyr Pro Leu Thr Asp Tyr
545                 550                 555

<210> SEQ ID NO 14
<211> LENGTH: 499
<212> TYPE: PRT
<213> ORGANISM: Homo sapiens

<400> SEQUENCE: 14

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

```
Pro Cys Gln Pro Leu Val Pro Leu Ser Trp Glu Asn Val Thr Val
            340                 345                 350

Asp Lys Val Leu Glu Phe Pro Leu Lys Gly His Pro Asn Leu Cys
            355                 360                 365

Val Gln Val Asn Ser Ser Glu Lys Leu Gln Leu Gln Glu Cys Leu Trp
370                 375                 380

Ala Asp Ser Leu Gly Pro Leu Lys Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
                420                 425                 430

Glu Tyr Leu Leu Gln Asp Leu Ser Gly Gln Cys Leu Gln Leu Trp
            435                 440                 445

Asp Asp Asp Leu Gly Ala Leu Trp Ala Cys Pro Met Asp Lys Tyr Ile
            450                 455                 460

His Lys Arg Trp Ala Leu Val Trp Leu Ala Cys Leu Leu Phe Ala Ala
465                 470                 475                 480

Ala Leu Ser Leu Ile Leu Leu Leu Lys Lys Asp His Ala Lys Gly Pro
                485                 490                 495

Gln Pro Gly

<210> SEQ ID NO 15
<211> LENGTH: 21
<212> TYPE: RNA
<213> ORGANISM: Homo sapiens

<400> SEQUENCE: 15
acuacacgcu caaggcccau u                                          21

<210> SEQ ID NO 16
<211> LENGTH: 21
<212> TYPE: RNA
<213> ORGANISM: Homo sapiens

<400> SEQUENCE: 16
ugggccuuga gcguguaguu u                                          21

<210> SEQ ID NO 17
<211> LENGTH: 21
<212> TYPE: RNA
<213> ORGANISM: Homo sapiens

<400> SEQUENCE: 17
acgcucaagg cccagggccu u                                          21

<210> SEQ ID NO 18
<211> LENGTH: 21
<212> TYPE: RNA
<213> ORGANISM: Homo sapiens

<400> SEQUENCE: 18
ggcccugggc cuugagcguu u                                          21

<210> SEQ ID NO 19
<211> LENGTH: 21
<212> TYPE: RNA
<213> ORGANISM: Homo sapiens
```

```
<400> SEQUENCE: 19
cugucacggu gcuccuggau u                                              21

<210> SEQ ID NO 20
<211> LENGTH: 21
<212> TYPE: RNA
<213> ORGANISM: Homo sapiens

<400> SEQUENCE: 20
uccaggagca ccgugacagu u                                              21

<210> SEQ ID NO 21
<211> LENGTH: 21
<212> TYPE: RNA
<213> ORGANISM: Homo sapiens

<400> SEQUENCE: 21
cucugucacg gugcuccugu u                                              21

<210> SEQ ID NO 22
<211> LENGTH: 21
<212> TYPE: RNA
<213> ORGANISM: Homo sapiens

<400> SEQUENCE: 22
caggagcacc gugacagagu u                                              21

<210> SEQ ID NO 23
<211> LENGTH: 20
<212> TYPE: DNA
<213> ORGANISM: Homo sapiens

<400> SEQUENCE: 23
ctacaagctg tccccagagg                                                20

<210> SEQ ID NO 24
<211> LENGTH: 15
<212> TYPE: DNA
<213> ORGANISM: Homo sapiens

<400> SEQUENCE: 24
ccgtccgtgg tgctg                                                     15

<210> SEQ ID NO 25
<211> LENGTH: 21
<212> TYPE: DNA
<213> ORGANISM: Homo sapiens

<400> SEQUENCE: 25
ggccaaagtc aacatcttct t                                              21

<210> SEQ ID NO 26
<211> LENGTH: 20
<212> TYPE: DNA
<213> ORGANISM: Homo sapiens

<400> SEQUENCE: 26
ggggtatatt cccaccaaca                                                20

<210> SEQ ID NO 27
<211> LENGTH: 21
<212> TYPE: DNA
<213> ORGANISM: Homo sapiens
```

```
<400> SEQUENCE: 27
acctgttcct gtgactgtac c                                          21

<210> SEQ ID NO 28
<211> LENGTH: 21
<212> TYPE: DNA
<213> ORGANISM: Homo sapiens

<400> SEQUENCE: 28
atgggttcac tttccgcaag g                                          21
```